(12) United States Patent
Bardotti et al.

(10) Patent No.: US 9,803,030 B2
(45) Date of Patent: Oct. 31, 2017

(54) MODIFIED SACCHARIDES

(75) Inventors: Angela Bardotti, Siena (IT); Francesco Berti, Siena (IT); Paolo Costantino, Siena (IT); Alessandro Pianigiani, legal representative, Siena (IT)

(73) Assignee: GLAXOSMITHKLINE BIOLOGICALS SA (BE)

( * ) Notice: Subject to any disclaimer, the term of this patent is extended or adjusted under 35 U.S.C. 154(b) by 236 days.

(21) Appl. No.: 12/448,709

(22) PCT Filed: Jan. 11, 2008
(Under 37 CFR 1.47)

(86) PCT No.: PCT/IB2008/001116
§ 371 (c)(1),
(2), (4) Date: Nov. 6, 2009

(87) PCT Pub. No.: WO2008/084411
PCT Pub. Date: Jul. 17, 2008

(65) Prior Publication Data
US 2010/0322958 A1    Dec. 23, 2010

(30) Foreign Application Priority Data
Jan. 11, 2007 (GB) .................................. 0700562.2

(51) Int. Cl.
*C08B 37/00* (2006.01)
*A61K 39/095* (2006.01)
*A61K 47/48* (2006.01)
*C07H 13/00* (2006.01)
*A61K 39/00* (2006.01)

(52) U.S. Cl.
CPC ............ *C08B 37/00* (2013.01); *A61K 39/095* (2013.01); *A61K 47/4833* (2013.01); *C07H 13/00* (2013.01); *C08B 37/006* (2013.01); A61K 2039/55505 (2013.01); A61K 2039/6037 (2013.01)

(58) Field of Classification Search
CPC ............ A61K 39/02; A61K 2039/6037; A61K 2039/6087; A61K 47/48; A61K 39/095; A61K 31/70; A61K 31/7024; A61K 38/16; A61K 39/385; A61K 31/715; C07K 14/195; C07K 14/00; C07K 14/34; C08B 37/00; C07H 11/04; C07H 11/00; C07H 13/02; C07H 13/12; C07H 15/04; C07H 5/06; A61P 31/04; A61P 37/04
See application file for complete search history.

(56) References Cited

FOREIGN PATENT DOCUMENTS

| WO | WO 03/080678 | * 10/2003 | ............. C08B 37/00 |
|---|---|---|---|
| WO | WO 2004/019992 | 3/2004 | |
| WO | WO 2006097851 A2 | * 9/2006 | ........... A61K 39/095 |
| WO | WO 2006/120576 | 11/2006 | |

OTHER PUBLICATIONS

Berry, D. S., Lynn, F., Lee, C. H., Frasch, C. E., & Bash, M. C. (2002). Effect of O acetylation of Neisseria meningitidis serogroup A capsular polysaccharide on development of functional immune responses. Infection and immunity, 70(7), 3707-3713.*
Kochetkov, N. K. (1984). Synthesis of fragments of bacterial polysaccharides and their application for the preparation of synthetic antigens. Pure. Appl. Chem, 56, 923-938.*
Lupisan, et al., Meningococcal Polysaccharide A O-Acetylation Levels Do Not Impact the Immunogenicity of the Quadrivalent Meningococcal Tetanus Toxoid Conjugate Vaccine: Results from a Randomized, Controlled Phase III Study of Healthy Adults Aged 18 to 25 Years, Clinical and Vaccine Immunology, Oct. 2013, pp. 1499-1507, vol. 20, No. 10.

* cited by examiner

*Primary Examiner* — Shaojia Anna Jiang
*Assistant Examiner* — Dale R Miller
(74) *Attorney, Agent, or Firm* — Lisa Matovcik

(57) ABSTRACT

Modified capsular saccharides comprising a blocking group at a hydroxyl group position on at least one of the monosaccharide units of the corresponding native capsular saccharide, wherein the blocking group is of the formula (Ia) or (Ib): —OX—Y (Ia) or —O—$R^1$ (Ib) wherein X is C(O), S(O) or $SO_2$; Y is $NR^1R^2$ or $R^3$; $R^1$ is $C_{1-6}$ alkyl substituted with 1, 2 or 3 groups independently selected from hydroxyl, sulphydryl and amine; $R^2$ is H or $C_{1-6}$ alkyl; and $R^3$ is $C_{1-6}$ alkyl; processes for modifying a capsular saccharide with the blocking groups; saccharide-protein conjugates comprising the modified capsular saccharide; processes for making the saccharide-protein conjugates, pharmaceutical compositions comprising the modified capsular saccharides and/or saccharide-protein conjugates; and methods and uses of the same.

19 Claims, 9 Drawing Sheets

Chemical Shift (ppm)

MODIFIED SACCHARIDES

RELATED APPLICATIONS

This application is the U.S. National Phase of International Application No. PCT/IB2008/001116, filed Jan. 11, 2008 and published in English, which claims priority to Great Britain Application No. 0700562.2 filed Jan. 11, 2007. The teachings of the above applications are incorporated in their entirety by reference.

All documents cited herein are incorporated by reference in their entirety.

TECHNICAL FIELD

This invention is in the field of polysaccharide chemistry and relates to modified saccharides, processes for their preparation, and conjugated derivatives. In particular, the invention relates to modified saccharides having improved stability in water.

BACKGROUND ART

Polysaccharides are important biological molecules and they have been widely used in the pharmaceutical industry for the prevention and treatment of diseases. For example, capsular polysaccharides have been used for many years in vaccines against capsulated bacteria, such as meningococcus (*Neisseria meningitidis*), pneumococcus (*Streptococcus pneumoniae*) and Hib (*Haemophilus influenzae* type B).

To enhance immunogenicity of these polysaccharides, particularly in children, conjugate vaccines were developed. These comprise a capsular polysaccharide conjugated to a carrier protein [e.g. references 1, 2, 3]. Conjugation can make T-independent antigens into T-dependent antigens.

A problem with many types of polysaccharide is poor stability in water. The stability of polysaccharides in water can depend on the nature of the β-glycosidic bonds joining the saccharide units. Poor stability in water is a result of the O-glycosidic bonds being readily hydrolysed in the presence of acids or glycosidases. The capsular polysaccharide of serogroup A meningococcus is an example of a polysaccharide having poor stability in water.

The stability of polysaccharides is a particular problem in the manufacture of conjugate vaccines. In order to prepare a polysaccharide-protein conjugate, it is necessary to manipulate chemically functional groups on the polysaccharide so that the polysaccharide may be linked to a protein. The exposure of a polysaccharide to chemical reagents in processes for doing this, and particularly to acids, may result in undesirable cleavage of glycosidic linkages and consequent fragmentation of the polysaccharide. Such fragmentation is highly undesirable, causing loss in yields in the synthesis of polysaccharide-protein conjugates.

Polysaccharides which are unstable in this way generally require careful choice of reagents and conditions to circumvent the problems described above. However, this limits the reagents available for manipulating the polysaccharide, thus limiting the range of linkages that may be made between the polysaccharide and carrier protein. In addition, the instability of these polysaccharides means it is difficult to develop robust procedures, which can be used to prepare vaccines on an industrial scale.

Reference 4 discloses a modified capsular saccharide comprising a blocking group at a hydroxyl group position on at least one of the monosaccharide units of the corresponding native capsular saccharide. The modified capsular saccharide is said to have improved stability to hydrolysis. It is an object of the invention to provide alternative or improved modified capsular saccharides that have improved stability to hydrolysis.

DISCLOSURE OF THE INVENTION

The invention is based on the discovery that modification of hydroxyl groups on monosaccharide units of capsular saccharides with specific blocking groups offers improved stability. Modified saccharides obtained by the process of the invention are more stable to hydrolysis than their native saccharide counterparts.

The present invention therefore provides a modified capsular saccharide comprising a blocking group at a hydroxyl group position on at least one of the monosaccharide units of the corresponding native capsular saccharide. The blocking group is defined below. The modified capsular saccharide of the present invention is more stable to hydrolysis than its native saccharide counterparts. Preferably, the modified capsular saccharide of the present invention retains immunological cross-reactivity with its native saccharide counterpart.

The present invention also provides processes for modifying a capsular saccharide with the blocking group; saccharide-protein conjugates comprising the modified capsular saccharide; processes for making the saccharide-protein conjugates, pharmaceutical compositions comprising the modified capsular saccharides and/or saccharide-protein conjugates; and methods and uses of the same.

Modified Saccharides of the Invention

The invention provides a modified capsular saccharide comprising a blocking group at a hydroxyl group position on at least one of the monosaccharide units of the corresponding native capsular saccharide. The blocking group is of the formula (Ia) or (Ib):

(Ia)

(Ib)

wherein
X is C(O); S(O) or $SO_2^-$;
Y is $NR^1R^2$ or $R^3$;
$R^1$ is $C_{1-6}$ alkyl substituted with 1, 2 or 3 groups independently selected from hydroxyl, sulphydryl and amine;
$R^2$ is H or $C_{1-6}$ alkyl; and
$R^3$ is $C_{1-6}$ alkyl.

Preferably, the blocking group is of formula (Ia). In this embodiment, it is preferred that X is C(O). Such carbamate and ester blocking groups have a stabilizing effect on the glycosidic bond and may be prepared under mild conditions. Examples of processes for manipulating a saccharide to provide carbamate and ester blocking groups are described below. However, the invention is not limited to modified saccharides prepared by the processes exemplified herein, and other processes for preparing modified saccharides of the invention will be readily apparent to the skilled person.

Preferably, $R^2$ is H.

The $C_{1-6}$ alkyl of $R^1$ is substituted with 1, 2 or 3 groups independently selected from hydroxyl, sulphydryl and amine. When the $C_{1-6}$ alkyl is substituted with 2 or 3 groups, the substitutions may be with the same group or different groups, although typically they will be with the same group. Preferably, the $C_{1-6}$ alkyl of $R^1$ is substituted with 1, 2 or 3 hydroxyl groups.

$R^1$ may be substituted at any position along the $C_{1-6}$ alkyl chain. Preferably, at least one substitution is present at the distal end of the $C_{1-6}$ alkyl chain. Where the $C_{1-6}$ alkyl chain is, a straight chain alkyl group, this means that the $C_{1-6}$ alkyl is substituted at $C_x$, wherein x is the total number of carbon atoms in the $C_{1-6}$ alkyl chain. Similarly, where the $C_{1-6}$ alkyl chain is a branched chain alkyl group, this means that the $C_{1-6}$ alkyl is substituted at the distal end of one of the branches, typically the longest branch.

In preferred embodiments, $R^1$ is substituted with a single group, this substitution being at the distal end of the $C_{1-6}$ alkyl chain, as discussed above. Such groups are particularly effective at providing improved stability to hydrolysis. Preferably, the single group is a hydroxyl group. Preferred groups therefore include hydroxymethyl, 2-hydroxyethyl, 3-hydroxypropyl, 4-hydroxybutyl, 5-hydroxypentyl and 6-hydroxyhexyl. A particularly preferred group is 2-hydroxyethyl.

In other preferred embodiments, $R^1$ is substituted with two vicinal groups, i.e. two groups at adjacent positions along the $C_{1-6}$ alkyl chain. Such groups are particularly effective at providing improved stability to hydrolysis. Preferably, the two vicinal groups are at the distal end of the $C_{1-6}$ alkyl chain. Where the $C_{1-6}$ alkyl chain is a straight chain alkyl group, this means that the two vicinal groups are at $C_x$ and $C_{x-1}$ wherein x is the total number of carbon atoms in the $C_{1-6}$ alkyl chain. Similarly, where the $C_{1-6}$ alkyl chain is a branched chain alkyl group, this means that the two vicinal groups are at the distal end of one of the branches, typically the longest branch. Preferably, the two vicinal groups are hydroxyl groups. Such groups provide a handle for conjugation to a carrier molecule, as discussed below. Preferred groups therefore include 1,2-dihydroxyethyl; 1,2-dihydroxypropyl and 2,3-dihydroxypropyl; 1,2-dihydroxybutyl, 2,3-dihydroxybutyl and 3,4-dihydroxybutyl; 1,2-dihydroxypentyl, 2,3-dihydroxypentyl, 3,4-dihydroxypentyl and 4,5-dihydroxypentyl; and 1,2-dihydroxyhexyl, 2,3-dihydroxyhexyl, 3,4-dihydroxyhexyl, 4,5-dihydroxyhexyl and 5,6-dihydroxyhexyl. As noted above, it is preferred that the two vicinal groups are at the distal end of the $C_{1-6}$ alkyl chain. Particularly preferred groups therefore include 1,2-dihydroxyethyl, 2,3-dihydroxypropyl; 3,4-dihydroxybutyl, 4,5-dihydroxypentyl and 5,6-dihydroxyhexyl. A particularly preferred group is 4,5-dihydroxypentyl.

In some embodiments, the modified capsular saccharide comprises at least two kinds of blocking group (as described above). For example, it is preferred for the saccharide to comprise a) at least one blocking group wherein $R^1$ is substituted with a single group, this substitution being at the distal end of the $C_{1-6}$ alkyl chain (as described above); and b) at least one blocking group wherein $R^1$ is substituted with two vicinal groups (as described above). Such mixed blocking groups are particularly effective at providing improved stability to hydrolysis. Moreover, by including at least one blocking group wherein $R^1$ is substituted with two vicinal hydroxyl groups, there is provided a handle for conjugation to a carrier molecule, as discussed below.

Preferably, $R^3$ is $C_1$-$C_3$ alkyl. Most preferably $R^3$ is $C_1$ alkyl ($CH_3$), although $C_2$ alkyl and $C_3$ alkyl are also preferred.

The blocking groups of formula —O—X—Y or —O—$R^1$ may be prepared from hydroxyl groups (e.g. as found in the native molecule) by standard derivatizing procedures, such as reaction of the hydroxyl group with an acyl halide, alkyl halide, sulfonyl halide etc. Hence, the oxygen atom in —O—X—Y is preferably the oxygen atom of the hydroxyl group, while the —X—Y group in —O—X—Y preferably replaces the hydrogen atom of the hydroxyl group. Alternatively, the blocking groups may be accessible via a substitution reaction, such as a Mitsunobu-type substitution. These and other methods of preparing blocking groups from hydroxyl groups are well known.

Typically, the modified saccharides of the present invention are oligosaccharides. Oligosaccharides may be obtained from polysaccharides by any of the depolymerising and sizing methods described herein.

The modified capsular saccharides of this invention are obtainable from native capsular saccharides. However, the present invention is not limited to modified saccharides obtained from native capsular saccharides. The modified capsular saccharides of the present invention may be obtained by other methods, such as total or partial synthesis (see, for example, reference 5).

In the modified capsular saccharides of the invention, the number of monosaccharide units having blocking groups may vary. Preferably, all or substantially all the monosaccharide units of the modified capsular saccharide may have blocking groups. Alternatively, at least 1%, 2%, 3%, 4%, 5%, 6%, 7%, 8%, 9%, 10%, 20%, 30%, 40%, 50%, 60%, 70%, 80% or 90% of the monosaccharide units of the modified capsular saccharide may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monosaccharide units of the modified capsular saccharide may have blocking groups.

Where the modified capsular saccharide comprises at least two kinds of blocking group, the number of monosaccharide units having each kind of blocking group may also vary. For example, the proportion of the total number of blocking groups made up by one type of blocking group relative to the other type(s) of blocking group may vary. In particular, when there are two kinds of blocking group present, the ratio of one type of blocking group to the other type of blocking group may be selected from 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2 and 1:1. In particular, in the embodiment described above where the saccharide comprises a) at least one blocking group wherein $R^1$ is substituted with a single group, this substitution being at the distal end of the $C_{1-6}$ alkyl chain; and b) at least one blocking group wherein $R^1$ is substituted with two vicinal groups, it is preferred that the ratio of the former type of blocking group to the latter type of blocking group is selected from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19 and 80:20. Of these ratios, 95:5, 94:6, 93:7, 92:8, 91:9, 90:10, 89:11, 88:12, 87:13, 86:14 and 85:15 are particularly preferred. Of these, 90:10 is preferred.

Likewise, the number of blocking groups on a monosaccharide unit may vary. For example, the number of blocking groups on a monosaccharide unit may be 1, 2, 3, 4, 5 or 6, preferably 1-4, more preferably 1 or 2, most preferably 1.

In one embodiment, the at least one monosaccharide unit having a blocking group includes a non-terminal monosaccharide unit. The term "non-terminal monosaccharide unit" means a monosaccharide unit that is not one of the terminal monosaccharide units in the oligosaccharide/polysaccharide chain.

This invention encompasses modified capsular saccharides wherein all the hydroxyl group positions of the terminal and non-terminal monosaccharide units have a blocking group. However, in some preferred embodiments there is at least one free hydroxyl group or amino group in the modified capsular saccharide of the present invention. A free hydroxyl group or amino group is advantageous because it provides a handle for further reactions of the modified capsular saccharide e.g. for conjugation to a carrier molecule, as discussed below. When the modified saccharide contains a free hydroxyl group, it may be an anomeric hydroxyl group, particularly a terminal anomeric hydroxyl group. When the modified saccharide contains an amino group, it may be derived from an anomeric hydroxyl group. Amino groups are readily accessible from anomeric hydroxyl groups by reductive amination (using, for example, $NaBH_3CN/NH_4Cl$). Similarly, in other preferred embodiments, there is at least one monosaccharide unit of the modified capsular saccharide where two vicinal hydroxyl groups of the corresponding native capsular saccharide do not comprise blocking groups. Preferably, 1%, 2%, 3%, 4%, 5%, 6%, 7%, 8%, 9%, 10%, 11%, 12%, 13%, 14%, 15%, 16%, 17%, 18%, 19% or 20% of the monosaccharide units have two vicinal hydroxyl groups in this way. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monosaccharide units have two vicinal hydroxyl groups in this way. Preferably, between 5-15%, most preferably 10%, of the monosaccharide units have two vicinal hydroxyl groups in this way. The two vicinal hydroxyl groups in the monosaccharide unit(s) are advantageous because they provide a handle for conjugation to a carrier molecule, as discussed below.

Alternatively, in some preferred embodiments, at least one or at least 1%, 2%, 3%, 4%, 5%, 6%, 7%, 8%, 9%, 10%, 11%, 12%, 13%, 14%, 15%, 16%, 17%, 18%, 19% or 20% of the monosaccharide units of the modified capsular saccharide have blocking groups wherein $R^1$ is substituted with two vicinal hydroxyl groups, as described above. For example, 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39 or 40 monosaccharide units of the modified capsular saccharide may have such blocking groups. Preferably, between 5-15%, most preferably 10%, of the monosaccharide units of the modified capsular saccharide have blocking groups wherein $R^1$ is substituted with two vicinal hydroxyl groups. Once again, the two vicinal hydroxyl groups in the monosaccharide unit(s) are advantageous because they provide a handle for conjugation to a carrier molecule, as discussed below.

It has been suggested in reference 4 that effective blocking groups are electron-withdrawing groups. Without wishing to be bound by theory, it is believed that glycosidic bonds are unstable to hydrolysis due to assistance from an intramolecular nucleophilic attack of a saccharide hydroxyl group on the glycosidic linkage (i.e. by formation of a cyclic intermediate). The greater the nucleophilicity of the hydroxyl group, the greater the tendency for intramolecular nucleophilic attack. An electron-withdrawing blocking group has the effect of delocalizing the oxygen lone pair, thereby decreasing the oxygen nucleophilicity and decreasing the tendency for intramolecular nucleophilic attack. Surprisingly, it has been found that groups comprising $C_{1-6}$ alkyl substituted with 1, 2 or 3 groups independently selected from hydroxyl, sulphydryl and amine can be effective blocking groups, despite the presence of the nucleophilic hydroxyl, sulphydryl or amine in the blocking group. Moreover, these hydroxyl-, sulphydryl- or amine-substituted groups are advantageous, as they allow for more effective conjugation of the modified capsular saccharide to a carrier molecule. Without wishing to be bound by theory, it is believed that this effect arises from the relative hydrophilicity of groups comprising $C_{1-6}$ alkyl substituted with 1, 2 or 3 groups independently selected from hydroxyl, sulphydryl and amine. Furthermore, where the blocking group comprises $C_{1-6}$ alkyl substituted with two vicinal hydroxyl groups, the blocking group itself provides a handle for conjugation to a carrier molecule.

In all the embodiments described above, the modified capsular saccharide is preferably a modified capsular saccharide having phosphodiester linkages. More preferably, the modified capsular saccharide is a modified *Neisseria meningitidis* serogroup A saccharide. *Neisseria meningitidis* serogroup A saccharides are particularly unstable to hydrolysis.

When the modified capsular saccharide is a modified *Neisseria meningitidis* serogroup A saccharide, the blocking group is preferably at the 4- and/or 3-positions, more preferably the 4-position, of the corresponding *Neisseria meningitidis* serogroup A saccharide. Blocking groups in the 4- and/or 3-positions *Neisseria meningitidis* serogroup A saccharide have been shown to be particularly efficacious for improving stability towards hydrolysis.

In embodiments with ester blocking groups (i.e. when the blocking group is of formula (Ia), X is C(O) and Y is $R^3$), the inventors have found that stability of a modified *Neisseria meningitidis* serogroup A saccharide is influenced by the proportion of 4- and/or 3-positions that have blocking groups. For example, the proportion of 4-positions that have blocking groups may be about 0%, at least 10%, 20%, 30%, 40%, 50%, 60%, 70%, 80%, 90%, 95% or about 100%, with at least 30% and about 100% being preferred. Similarly, the proportion of 3-positions that have blocking groups may be about 0%, at least 10%, 20%, 30%, 40%, 50%, 60%, 70%, 80%, 90%, 95% or about 100%, with at least 95% and about 100% being preferred. Typically, the proportion of 4- and 3-positions that have blocking groups is about the same at each position. In other words, the ratio of 4-positions that have blocking groups to 3-positions that have blocking groups is about 1:1. However, in some embodiments, the proportion of 4-positions that have blocking groups may vary relative to the proportion of 3-positions that have blocking groups. For example, the ratio of 4-positions that have blocking groups to 3-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2. Similarly, the ratio of 3-positions that have blocking groups to 4-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2.

This invention also provides a saccharide of the formula:

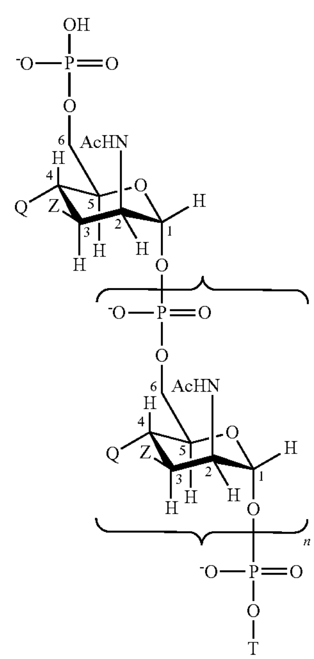

wherein
T is of the formula (A) or (B):

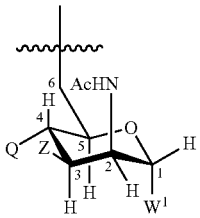
(A)

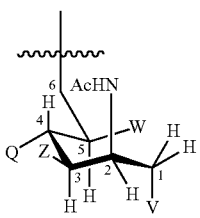
(B)

n is an integer from 1 to 100;
each Z group is independently selected from —OH, OAc or a blocking group as defined above; and
each Q group is independently selected from —OH, OAc or a blocking group as defined above;
V is selected from —NH$_2$, —NHE, —NE$^1$E$^2$, W$^2$, or —O-D, where: E, E$^1$ and E$^2$ are nitrogen protecting groups, which may be the same or different, and D is an oxygen protecting group;
W is selected from —OH or a blocking group as defined above;
W$^1$ is selected from —OH or a blocking group as defined above;
W$^2$ is selected from —OH or a blocking group as defined above.
and wherein at least one (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) of the Z groups and/or at least one (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) of the Q groups are blocking groups as defined above.
Preferably, n is an integer from 15 to 25.
Each of the n+2 Z groups may be the same or different from each other. Likewise, each of the n+2 Q groups may be the same or different from each other.
V is preferably —NH$_2$ or —NHE.
Suitable nitrogen protecting groups are silyl groups (such as TMS, TES, TBS, TIPS), acyl derivatives (such as trifluoroacetamides, methoxycarbonyl, ethoxycarbonyl, t-butoxycarbonyl (Boc), benzyloxycarbonyl (Z or Cbz), 9-fluorenylmethoxycarbonyl (Fmoc), 2-(trimethylsilyl)ethoxy carbonyl, allyloxycarbonyl (Alloc), 2,2,2-trichloroethoxycarbonyl (Troc)), sulfonyl derivatives (such as β-trimethylsilylethanesulfonyl (SES)), sulfenyl derivatives, C$_{1-12}$ alkyl, benzyl, benzhydryl, trityl, allyl, 9-phenylfluorenyl, etc. A preferred nitrogen protecting group is Fmoc.
Divalent nitrogen protecting groups, which can be used as E$^1$E$^2$, include cyclic imide derivatives (such as N-phthalimides, N-dithiasuccinimides, N-2,3-diphenylmaleimides), imine derivatives (such as N-1,1-dimethylthiomethyleneamines, N-benzylideneamines, N-p-methoxybenzylideneamines, N-diphenylmethyleneamines), enamine derivatives (such as N-(5,5-dimethyl-3-oxo-1-cyclohexenyl)amines), etc. A preferred divalent nitrogen protecting group is N-phthalimidyl.

Suitable oxygen protecting groups include esters, ethers (e.g. silyl ethers or alkyl ethers) and acetals. Specific examples include allyl, acetyl, Aloc, benzyl, benzyloxymethyl (BOM), t-butyl, trityl, tert-butyldimethylsilyl (TBS), tert-butyldiphenylsilyl (TBDPS), triethylsilyl (TES), trimethylsilyl (TMS), tri-isopropylsilyl (TIPS), paramethoxybenzyl (PMB), MEM, methoxymethyl (MOM), MTM and tetrahydropyranyl (THP).

All the Z groups may be OH (subject to at least one of the Z groups and/or at least one of the Q groups being blocking groups). As an alternative to all the Z groups being OH, at least 10%, 20%, 30%, 40%, 50%, 60%, 70%, 80% or 90% of the Z groups may be OAc. Preferably, about 60-90% of the Z groups are OAc, with the remainder of the Z groups being OH or blocking groups as defined above. Preferably, at least 1%, 2%, 3%, 4%, 5%, 6%, 7%, 8%, 9%, 10%, 15%, 20%, 25%, 30%, 35% or 40% of the Z groups are blocking groups, 60-90% are OAc and the remainder are OH. Preferably, about 10-40% of the Z groups are blocking groups, 60-90% are OAc and the remainder are OH. Alternatively, about 0%, at least 10%, 20%, 30%, 40%, 50%, 60%, 70%, 80%, 90%, 95% or about 100% of the Z groups are blocking groups, with at least 95% and about 100% being preferred.

All the Q groups may be OH (subject to at least one of the Z groups and/or Q groups being blocking groups). Alternatively, at least 1%, 2%, 3%, 4%, 5%, 6%, 7%, 8%, 9%, 10%, 15% or 20% of the Q groups may be OAc. Preferably, about 1-20% of Q groups are OAc, with the remainder of the Q groups being OH or blocking groups as defined above. Preferably, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% of the Q groups are blocking groups, 1-20% are OAc and the remainder are OH. Preferably, about 80-99% of the Q groups are blocking groups; 1-20% are OAc and the remainder are OH. Alternatively, about 0%, at least 10%, 20%, 30%, 40%, 50%, 60%, 70%, 80%, 90%, 95% or about 100% of the Q groups are blocking groups, with at least 30% and about 100% being preferred.

The invention also provides a molecule comprising a saccharide moiety of formula:

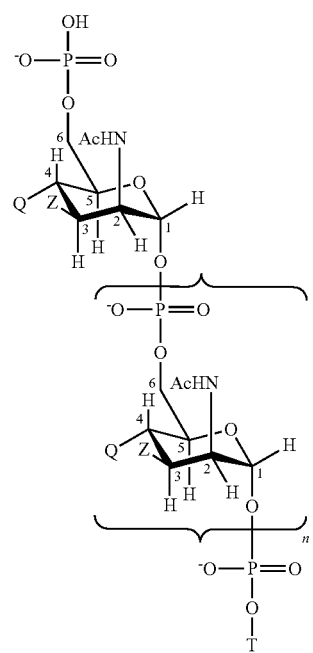

wherein
T is of the formula (A) or (B):

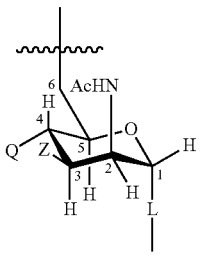

(A)

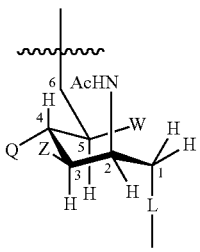

(B)

n, Z, Q and W are as defined above; at least one (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) of the Z groups and/or at least one (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) of the Q groups are blocking groups; and: L is O, NH, NE, S or Se.

The free covalent bond of L can be joined to any appropriate moiety e.g. to -H, -E, a linker, a protein carrier, etc. L is preferably N or O. It is also possible for L to be N, joined to a divalent linker, to a divalent protecting group, or to a divalent protein carrier.

Preferred identities of the n, Z, Q and W groups are described above.

This invention also provides a molecule comprising a saccharide of the formula:

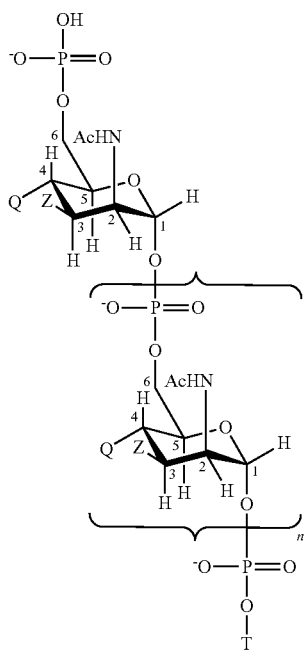

wherein
T is of the formula (A) or (B):

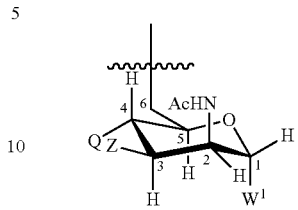

(A)

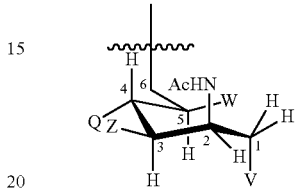

(B)

n, Z, Q, W, $W^1$ and V are as defined above, and at least one (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 15, 36, 37, 38, 39 or 40) of the Z groups and/or at least one (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) of the Q groups are of the formula (IIa) or IIb):

—O—X—Y' (IIa)

—O—$R^4$ (IIb)

wherein
X is as defined above;
Y' is $NR^2R^4$;
$R^2$ is as defined above; and
$R^4$ is —$C_{1-4}$ alkylene-CH(O) or —$C_{1-5}$ alkylene-NH—, wherein the —NH— group is part of a protein carrier.

Preferably; the at least one Z and/or Q group(s) are of formula (IIa). In this embodiment, it is preferred that X is C(O).

Preferred $R^2$ groups are described above in relation to formulae (Ia).

Preferred $R^4$ groups include —$C_1$ alkylene-CH(O), —$C_2$ alkylene-CH(O), —$C_3$ alkylene-CH(O) and —$C_4$ alkylene-CH(O). A particularly preferred $R^4$ group is —$C_3$ alkylene-CH(O).

Other preferred $R^4$ groups include —$C_1$ alkylene-NH—, —$C_2$ alkylene-NH—; —$C_3$ alkylene-NH—, —$C_4$ alkylene-NH— and —$C_5$ alkylene-NH—. A particularly preferred $R^4$ group is —$C_4$ alkylene-NH—.

Preferred identities of the n, Z, Q, W, $W^1$ and V groups are described above.

Process for Producing a Modified Saccharide.

The invention provides a process for modifying a capsular saccharide comprising the steps of:
(a) providing a capsular saccharide having at least one hydroxyl group on a monosaccharide unit; and
(b) converting said at least one hydroxyl group into a blocking group.

The blocking group is any of the blocking groups defined above.

The capsular saccharide may be a native capsular saccharide (oligosaccharide or polysaccharide). As an alternative, the capsular saccharide may be, for example, a de-O- acetylated capsular saccharide and/or a capsular saccharide having a terminal amino group (e.g. obtained by reductive amination).

A preferred process for modifying a saccharide wherein the blocking group is —OC(O)NR$^1$R$^2$ is when step (b) comprises the steps of:
- (b1) reacting the capsular saccharide with a bifunctional reagent in an organic solvent; and
- (b2) reacting the product of step (b1) with an amino compound of formula (III):

HNR$^1$R$^2$                                               (III)

wherein R$^1$ and R$^2$ are as defined above.

The term "bifunctional reagent" means any reagent that is capable of performing the dual functions of (i) providing in step (b1) a first electrophilic carbon atom for coupling with the hydroxyl group(s) on the saccharide; and (ii) providing a second electrophilic carbon atom for coupling with the amino group used in step (b2). Generally, the second electrophilic carbon atom is regenerated from the first electrophilic carbon atom during step (b). The bifunctional reagent provides a —C(O)— linkage between the polysaccharide and the amino compound.

Bifunctional reagents for use in the present invention include, but are not limited to, 1,1'-carbonyldiimidazole (CDI), carbonyl di-1,2,4-triazole (CDT), carbonyl di-1,2,3-benzotriazole (CDB), diphenylcarbonate, cyanogen bromide, phosgene or triphosgene. The skilled person will be aware of other bifunctional reagents that can perform the same function as these.

A preferred bifunctional reagent is CDI. CDI has the advantage of being a milder reagent than, for example, phosgene or cyanogen bromide. In particular, coupling reactions using CDI do not generate hydrohalic acid gases, such as HCl or HBr. The generation of HCl or HBr gas is undesirable, because these gases require scrubbing of the reaction chamber outlet to avoid their escape into the atmosphere. Moreover, the generation of HCl or HBr gas may affect sensitive functional groups on the saccharide, resulting in loss in yields due to decomposition or fragmentation of the saccharide.

The organic solvent used in step (b1) is preferably an aprotic solvent. Aprotic solvents are well known to the person skilled in the art and do not contain any ionizable hydrogen atoms. These solvents are advantageous because they facilitate the reaction of hydroxyl group(s) on the saccharide with the bifunctional reagent, by enhancing the nucleophilicity of the hydroxyl group(s). Suitable aprotic solvents include, but are not limited to, dimethylsulfoxide (DMSO), dimethylformamide (DMF), formamide, hexamethylphosphorus triamide (HMPT), 1,3-dimethyl-3,4,5,6-tetrahydro-2(1H)-pyrimidinone (DMPU), dimethylacetamide (DMAC), or hexamethylphosphoramide (HMPA). DMSO is preferred.

In step (b2) of the process of the invention, the product of step (b1) is reacted with an amino compound to form the modified polysaccharide. The amino compound used in the process of the present invention is of formula (III), as defined above.

Suitable amino compounds which may be used in the invention depend on R$^1$ and R$^2$. As described above, in preferred embodiments, R$^1$ is substituted with a single hydroxyl group, this substitution being at the distal, end of the C$_{1-6}$ alkyl chain, and R$^2$ is H. Preferred amino compounds which may be used in the invention therefore include aminomethanol, 2-aminoethanol, 3-aminopropan-1-ol, 4-aminobutan-1-ol, 5-aminopentan-1-ol and 6-aminohexyl-1-ol. A particularly preferred amino compound is 2-aminoethanol. In other preferred embodiments, R$^1$ is substituted with two vicinal hydroxyl groups and R$^2$ is H. Preferred amino compounds which may be used in the invention therefore include 1-aminoethane-1,2-diol; 1-aminopropane-1,2-diol and 3-aminopropane-1,2-diol; 1-aminobutane-1,2-diol, 1-aminobutane-2,3-diol and 4-aminobutane-1,2-diol; 1-aminopentane-1,2-diol, 1-aminopentane-2,3-diol, 5-aminopentane-2,3-diol and 5-aminopentane-1,2-diol; and 1-aminohexane-1,2-diol, 1-aminohexane-2,3-diol, 5-aminohexane-3,4-diol, 6-aminohexane-2,3-diol and 6-aminohexane-1,2-diol. In particularly preferred embodiments, R$^1$ is substituted with two vicinal hydroxyl groups at the distal end of the C$_{1-6}$ alkyl chain. Preferred amino compounds which may be used in the invention therefore include 3-aminopropane-1,2-diol, 4-aminobutane-1,2-diol, 5-aminopentane-1,2-diol and 6-aminohexane-1,2-diol. A particularly preferred amino compound is 5-aminopentane-1,2-diol. These may be used in the salt form (e.g. hydrochloride salt).

A preferred process of the invention is exemplified in Scheme 1 below:

Scheme 1

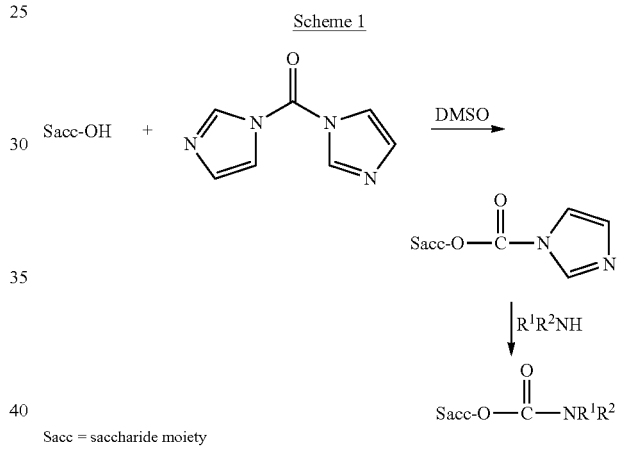

Sacc = saccharide moiety

In this scheme, the saccharide (e.g. MenA polysaccharide or oligosaccharide) is first activated through at least one of its hydroxyl groups on a monosaccharide unit using CDI in DMSO solvent. The resulting imidazole carbamate intermediate is trapped by the amine R$^1$R$^2$NH (e.g. 2-aminoethanol) to give the modified saccharide.

The modified saccharides may alternatively be prepared in a one-step process by reacting one or more hydroxyl groups on a capsular saccharide with a reagent of the formula XC(O)NR$^1$R$^2$, wherein X is a leaving group, and R$^1$ and R$^2$ are as defined above. Suitable leaving groups include, but are not limited to, —Cl, —Br, —CF$_3$, —OC$_6$F$_5$ or —CCl$_3$.

A preferred process for modifying a saccharide wherein the blocking group is —OC(O)R$^3$ is when step (b) comprises the step of:
- (b1) reacting the capsular saccharide with [(R$^3$C(O)]$_2$O in the presence of an imidazole catalyst.

This process is particularly suitable for modifying a saccharide wherein the blocking group is —OC(O)CH$_3$. In this embodiment, step (b) comprises the step of:
- (b1) reacting the capsular saccharide with [(CH$_3$C(O)]$_2$O (acetic anhydride) in the presence of an imidazole catalyst.

Alternatively, modified capsular saccharides of the present invention may be prepared by synthetic means, for example, from suitable monosaccharide units. Typically, total synthesis of a modified capsular saccharide comprises forming glycosidic linkages (e.g. phosphodiester linkages) between suitable monosaccharide units and then modifying the resultant saccharide in any manner described above. Alternatively, the monosaccharide units may be modified before forming the glycosidic linkages to provide the same modified capsular saccharide.

The modified capsular saccharides of this invention are preferably oligosaccharides. Starting from native capsular polysaccharides, modified capsular oligosaccharides may be obtained by either of two methods: (1) modifying the capsular polysaccharide followed by depolymerising and sizing the modified, polysaccharide to form a modified oligosaccharide; or (2) depolymerising and sizing the capsular polysaccharide followed by modifying the resultant oligosaccharide to form a modified oligosaccharide. Both methods are encompassed within the present invention. However, the first method is preferred in certain embodiments, since this method ensures that a terminal hydroxyl group will be available for subsequent conjugation of the modified oligosaccharide to a carrier molecule, such as a protein.

The present invention also provides a process for modifying a *Neisseria meningitidis* serogroup A polysaccharide comprising the steps of:

(a) providing a *Neisseria meningitidis* serogroup A polysaccharide;
(b) depolymerising and sizing said polysaccharide to provide an oligosaccharide; and
(c) converting at least one hydroxyl group of the oligosaccharide into a blocking group, as described above.

Step (b) of this process may optionally be followed by known derivatizing step(s) before step (c). Known derivatizing steps include, for example, reductive amination followed by protection of the resulting —$NH_2$ group and/or de-O-acetylation.

This invention also provides a process for modifying a *Neisseria meningitidis* serogroup A polysaccharide comprising the steps of:

(a) providing a *Neisseria meningitidis* serogroup A polysaccharide;
(b) converting at least one hydroxyl group of the polysaccharide into a blocking group, as described above; and
(c) depolymerising and sizing the resulting polysaccharide to provide an oligosaccharide.

Step (c) of this process may optionally be followed by known derivatizing step(s). Known derivatizing steps include, for example, reductive amination followed by protection of the resulting —$NH_2$— group and/or de-O-acetylation.

Any of the processes described above may be followed by a step in which contaminants (e.g. low molecular weight contaminants) are removed.

Capsular Saccharide Starting Materials

The modified capsular saccharides of the invention are obtainable from native capsular saccharides. The term "native capsular saccharide" refers to sugar-containing polymers (e.g. polymers of sugars, sugar acids, amino sugars, polyhydric alcohols, sugar alcohols, and sugar phosphates etc.) which may be found in the capsule of bacteria (both Gram-positive and Gram-negative) such as *N. meningitidis, S. pneumoniae* and *H. influenzae*. Furthermore, "native capsular saccharide" includes both polysaccharides and oligosaccharides. Native capsular oligosaccharides may be obtained by depolymerising and sizing native polysaccharides.

The "hydroxyl group position" of a native capsular saccharide is a position on the native capsular saccharide having a hydroxyl group. However, it does not include positions in glycosidic linkages, or the residues thereof, having hydroxyl groups (e.g. a hydroxyl group which is part of a phosphate linkage does not occupy a hydroxyl group position). Nor does it include positions where there is an acetoxy group (AcO) group on the native capsular saccharide are also not hydroxyl group positions.

The native capsular saccharide may comprise saccharide units linked by phosphodiester bonds. Saccharides comprising phosphodiester bonds may be unstable to hydrolysis.

The native capsular saccharide and the modified capsular saccharide of the invention are preferably immunogenic in mammals (e.g. humans). The mammal may be a human adult or a child.

The native capsular saccharide is preferably a polysaccharide (or oligosaccharide fragment thereof) from *N. meningitidis* (including serogroups A, B, C, W135 and Y), *S. pneumoniae* (including serotypes 1, 4, 5, 6B, 9V, 14, 18C, 19F and 23F), *H. influenzae* type B, *Neisseria gonorrhoeae, Streptococcus agalactiae, Escherichia coli, Salmonella typhi, Streptococcus mutans, Cryptococcus neoformans, Moraxella catarrhalis, Klebsiella pneumoniae, Staphylococcus aureus*, and/or *Pseudomonas aeruginosa*.

Although the invention may be applied to any serogroup of *N. meningitidis*, it is preferred to use a capsular saccharide from serogroup A ("MenA"). The MenA capsular saccharide is particularly unstable in aqueous solution, meaning that special procedures need to be used to perform chemical manipulations (e.g. conjugation to carrier proteins) on this molecule. However, MenA saccharides modified according to the invention are found to be advantageously stable in aqueous solution.

The MenA capsular polysaccharide {→6)-D-ManpNAc (3/4OAc)-α-(1→$OPO_3$→} is composed of N-acetylmannosamine residues linked together by α1-6 phosphodiester bonds having the repeat units shown below.

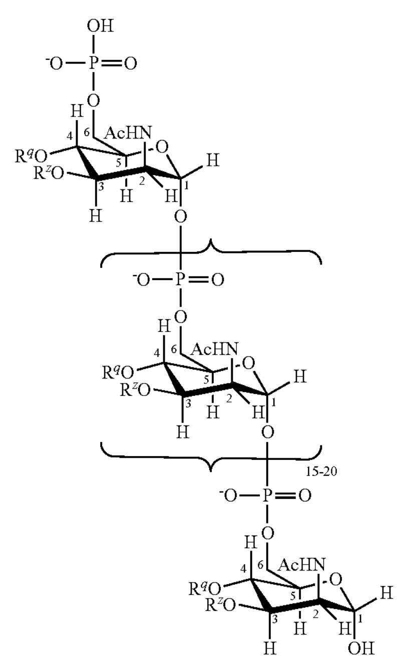

-continued $R^z = Ac$
$R^q = H$ } 60-90%

$R^z = H$
$R^q = H$ } 5-20%

$R^z = H$
$R^q = Ac$ } 1-20%

In accordance with the definitions above, about 80-99% of the 4-positions are hydroxyl group positions, and about 10-40% of the 3-positions are hydroxyl group positions. The terminal 1-hydroxy group also occupies a hydroxyl group position. The terminal 1-hydroxy group is a terminal anomeric hydroxyl group. The hydroxyl group which is part of the —OP(O)(OH)O⁻ group is not a hydroxyl group position.

Saccharide-Protein Conjugates

The modified saccharides of the invention may be subjected to any usual downstream processing which is applied to saccharides (e.g. derivatisation, conjugation, fragmentation, etc.). To enhance immunogenicity, modified saccharides of the invention are preferably conjugated to a carrier protein. Conjugation to carrier proteins is particularly useful for pediatric vaccines [6] and is a well known technique [e.g. reviewed in refs. 7 to 15 etc.]. The polysaccharide may be linked either directly to the protein [2, 16] or it may be linked via a linker group. Many different types of linker groups have been proposed for linking polysaccharides to proteins [e.g. 3, 17].

The invention thus provides a conjugate of a protein and a modified saccharide of the invention. The protein may be conjugated to the saccharide directly, or a linker may be used. Any suitable linker chemistry can be used. The improved stability of the modified polysaccharide advantageously allows a wide range of linkages to be used.

As described above, in some embodiments it is preferred that the modified capsular saccharide has at least one free hydroxyl group or amino group which can be used as a handle for subsequent linkage to a carrier protein.

A modified capsular saccharide having a free hydroxyl group may be obtained by selectively blocking hydroxyl groups on a capsular saccharide, or selectively de-blocking a modified capsular saccharide in which all the hydroxyl groups are blocked. Alternatively, a free hydroxyl group may be revealed by depolymerising and sizing a modified capsular saccharide. Preferably, the at least one free hydroxyl group is a terminal anomeric hydroxyl group. The terminal anomeric hydroxyl group is preferred as the free hydroxyl group because a terminal anomeric hydroxyl group may be revealed by depolymerising and sizing a modified capsular saccharide.

A modified capsular saccharide having a free amino group may be obtained by reductive amination of a terminal anomeric hydroxyl group, optionally followed by protection of the resulting —NH₂ group. The reductive amination reaction may be carried out before or after the modifying step of the present invention. Preferably, reductive amination is carried out before the modifying step of the present invention since the resulting —NH₂ group can be selectively protected/deprotected in the presence of hydroxyl groups/blocking groups.

For example, the present invention provides a process for making a saccharide-protein conjugate comprising the steps of:

(a) providing a modified capsular saccharide of the invention, wherein the modified saccharide comprises a terminal anomeric hydroxyl group or an amino group derived from a terminal anomeric hydroxyl group; and (b) linking the modified capsular saccharide to a protein via the terminal anomeric hydroxyl group or the amino group derived from a terminal anomeric hydroxyl group.

The protein is preferably a bacterial toxin or toxoid, in particular diphtheria toxin or toxoid. For example, the protein is preferably CRM₁₉₇.

Linkages via a linker group may be made using any known procedure, for example, the procedures described in references 3 and 17. A preferred type of linkage is a carbonyl linker, which may be formed by reaction of a free hydroxyl group of the modified saccharide with CDI [18, 19] followed by reaction with a protein to form a carbamate linkage. Another preferred type of linkage is an adipic acid linker, which may be formed by coupling a free —NH₂ group on the modified saccharide with adipic acid (using, for example, diimide activation), and then coupling a protein to the resulting saccharide-adipic acid intermediate. [11, 20, 21]. Other linkers include B-propionamido [22], nitrophenyl-ethylamine [23], haloacyl halides [24], glycosidic linkages [25], 6-aminocaproic acid [26], ADH [27], C₄ to C₁₂ moieties [28] etc.

Conjugation may involve: reduction of the anomeric terminus to a primary hydroxyl group, optional protection/deprotection of the primary hydroxyl group; reaction of the primary hydroxyl group with CDI to form a CDI carbamate intermediate; and coupling the CDI carbamate intermediate with an amino group on a protein.

Scheme 2 shows two different examples of how a capsular saccharide may be conjugated to a carrier protein, in accordance with the present invention. In the first example, the protein is conjugated via a terminal hydroxyl group. In the second example, the protein is linked via a terminal amino group.

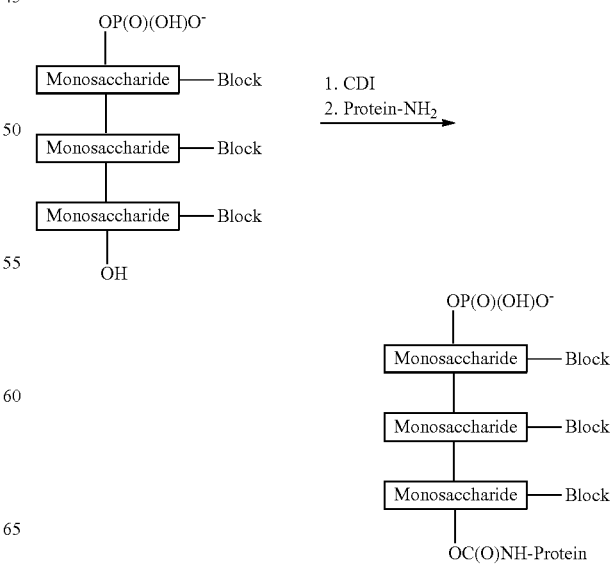

Scheme 2

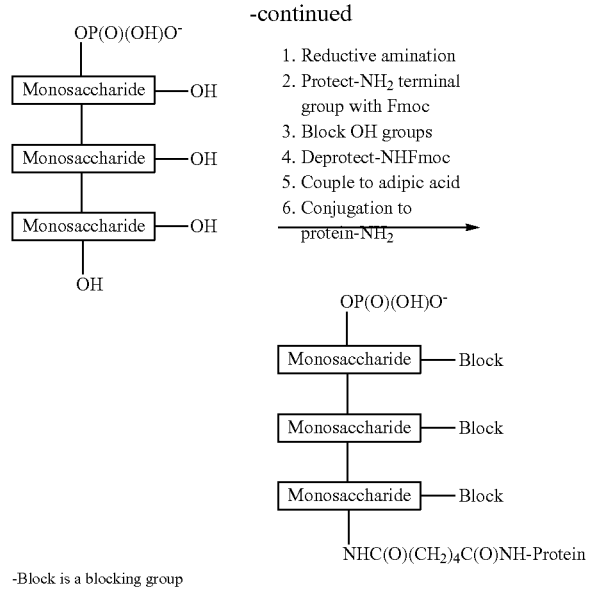

-Block is a blocking group

Direct linkages to the protein may comprise oxidation of the polysaccharide followed by reductive amination with the protein, as described in, for example, references 2 and 16. For example, in embodiments where there is at least one monosaccharide unit of the modified capsular saccharide where two vicinal hydroxyl groups of the corresponding native capsular saccharide do not comprise blocking groups, one or more pairs of vicinal hydroxyl groups may be converted into aldehyde groups by oxidative cleavage (e.g. $NaIO_4$, $Pb(OAc)_4$, etc.). The modified capsular saccharide may then be linked to the protein by reductive amination.

For example, the present invention provides a process for making a saccharide-protein conjugate comprising the steps of:
(a) providing a modified capsular saccharide of the invention wherein there is at least one monosaccharide unit of the modified capsular saccharide where two vicinal hydroxyl groups of the corresponding native capsular saccharide do not comprise blocking groups;
(b) converting at least one of the pairs of vicinal hydroxyl groups into aldehyde groups by oxidative cleavage; and
(c) linking the modified capsular saccharide to a protein by reductive amination.

The protein is preferably a bacterial toxin or toxoid, in particular diphtheria toxin or toxoid. For example, the protein is preferably $CRM_{197}$.

As described above, in some embodiments, it is preferred that at least one of the monosaccharide units of the modified capsular saccharide comprise blocking groups wherein $R^1$ is substituted with two vicinal hydroxyl groups. The two vicinal hydroxyl groups can be used as a handle for subsequent linkage to a carrier protein. For example, one or more pairs of vicinal hydroxyl groups may be converted into aldehyde groups by oxidative cleavage (e.g. $NaIO_4$, $Pb(OAc)_4$, etc.). The modified capsular saccharide may then be linked to the protein by reductive amination.

For example, the present invention provides a process for making a saccharide-protein conjugate comprising the steps of:
(a) providing a modified capsular saccharide of the invention wherein at least one of the monosaccharide units comprise blocking groups wherein $R^1$ is substituted with two vicinal hydroxyl groups;
(b) converting at least one of the pairs of vicinal hydroxyl groups into aldehyde groups by oxidative cleavage; and
(c) linking the modified capsular saccharide to a protein by reductive amination.

The protein is preferably a bacterial toxin or toxoid, in particular diphtheria toxin or toxoid. For example, the protein is preferably $CRM_{197}$.

In some embodiments of this process, all of the vicinal hydroxyl groups present in the blocking groups are converted into aldehyde groups in step (b). In these embodiments, the number of aldehyde groups produced depends on the total number of blocking groups wherein $R^1$ is substituted with two vicinal hydroxyl groups that are present in the modified capsular saccharide. In other embodiments, the conditions for oxidative cleavage are selected such that only a proportion of the vicinal hydroxyl groups present in the blocking groups are converted into aldehyde groups. In these embodiments, the number of aldehyde groups produced depends on the total number of blocking groups wherein $R^1$ is substituted with two vicinal hydroxyl groups that are present in the modified capsular saccharide and the conditions selected. In such embodiments, it is preferred that 1%, 2%, 3%, 4%, 5%, 6%, 7%, 8%, 9%, 10%, 11%, 12%, 13%, 14%, 15%, 16%, 17%, 18%, 19% or 20% of the monosaccharide units of the modified capsular saccharide to have blocking groups that are converted into aldehyde groups. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monosaccharide units have blocking groups that are converted into aldehyde groups. Preferably, between 5-15%, most preferably 10%, of the monosaccharide units have blocking groups that are converted into aldehyde groups.

Scheme 3 shows two further examples of how a capsular saccharide may be conjugated to a carrier protein, in accordance with the present invention. In the first example (left hand side), all of the blocking groups have an $R^1$ group that is substituted with two vicinal hydroxyl groups. A proportion (e.g. 10%) of these vicinal hydroxyl groups is converted into aldehyde groups for conjugation to a protein. In the second example (right hand side), two types of blocking group are present. A proportion of these (e.g. 10%) have an $R^1$ that is substituted with two vicinal hydroxyl groups. All of these vicinal hydroxyl groups are converted into aldehyde groups for conjugation to a protein.

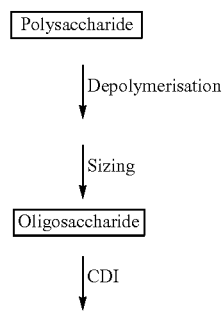

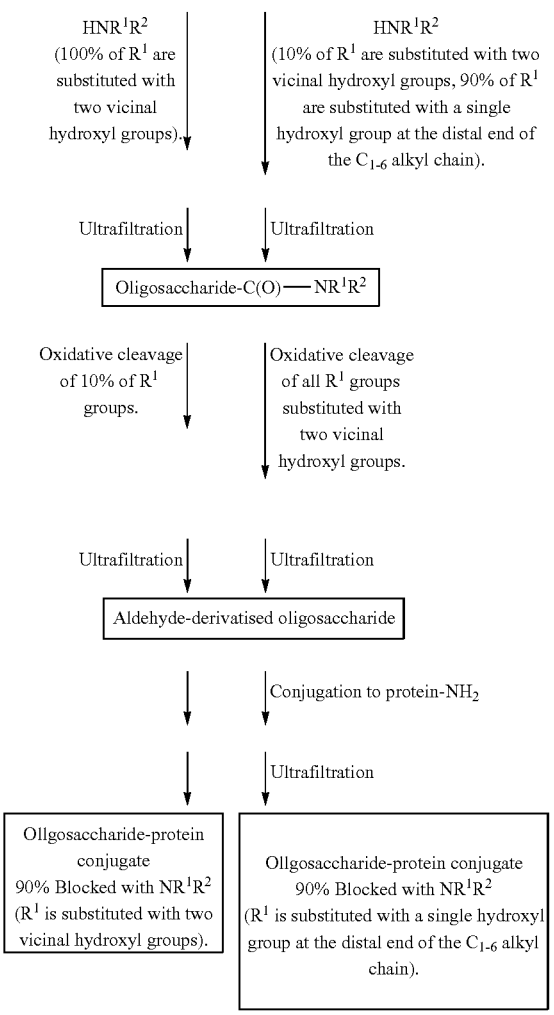

Preferred carrier proteins are bacterial toxins or toxoids, such as diphtheria or tetanus toxoids. These are commonly used in conjugate vaccines. The CRM$_{197}$ diphtheria toxoid is particularly preferred [29]. Other suitable carrier proteins include the *N. meningitidis* outer membrane protein [30], synthetic peptides [31,32], heat shock proteins [33,34], pertussis proteins [35,36], protein D from *H. influenzae* [37], cytokines [38], lymphokines [38], hormones [38], growth factors [38], toxin A or B from *C. difficile* [39], iron-uptake proteins [40] etc. It is possible to use mixtures of carrier proteins.

After conjugation, free and conjugated saccharides can be separated. There are many suitable methods, including hydrophobic chromatography, tangential ultrafiltration, diafiltration etc. [see also refs. 41, 42 etc.].

A single carrier protein may carry multiple different saccharides [43].

Pharmaceutical Compositions and Methods

Compositions made using the methods of the invention are pharmaceutically acceptable. They may include components in addition to the modified saccharide and/or conjugate e.g. they will typically include one or more pharmaceutical carrier(s). A thorough discussion of such components is available in reference 44. Thus the invention provides a pharmaceutical composition comprising (a) a modified saccharide of the invention and/or a conjugate of the invention, and (b) a pharmaceutically acceptable carrier. The composition is preferably an immunogenic composition (e.g. a vaccine). Vaccines based on saccharides or saccharide-protein conjugates are well known in the art.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [45], but keeping osmolality in this range is nevertheless preferred.

The pH of a composition will generally be between 5.0 and 80, and more typically between 5.5 and 6.5 e.g. between 6.5 and 7.5. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include a preservative such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred.

The composition may include material for a single immunisation, or may include material for multiple immunisations (i.e. a 'multidose' kit). The inclusion of a preservative is preferred in multidose arrangements.

Vaccines are typically administered in a dosage volume of about 0.5 ml.

Compositions are preferably stored at between 2° C. and 8° C. They should not be frozen. They should ideally be kept out of direct light.

Where a composition includes a conjugate then it may also comprise unconjugated carrier protein, but it is preferred that the amount of unconjugated carrier relative to the total amount of that carrier is less than 5%.

Compositions the invention are suitable for administration to human patients, and the invention provides a method of raising an immune response in a patient, comprising the step of administering such a composition to the patient. The invention also provides the compositions of the invention for use as medicaments. The invention also provides the use of a modified saccharide and/or of a conjugate of the invention, in the manufacture of a medicament for raising an immune response in a patient. The immune response raised by these methods and uses will generally include an antibody response, preferably a protective antibody response against meningococcal infection. Diseases caused by *Neisseria* include meningitis, septicaemia and gonorrhoea. The prevention and/or treatment of bacterial meningitis is preferred.

The compositions can be administered in various ways. The most preferred immunisation route is by intramuscular injection (e.g. into the arm or leg), but other available routes include subcutaneous injection, intranasal [46-48], oral [49], intradermal [50,51], transcutaneous, transdermal [52], etc.

Compositions prepared according to the invention may be used to treat both children and adults. The patient may be less than 1 year old, 1-5 years old, 5-15 years old, 15-55 years old, or at least 55 years old. The patient may be elderly (e.g. ≥50 years old, preferably ≥65 years), the young (e.g. ≤5 years old), hospitalised patients, healthcare workers, armed service and military personnel, pregnant women, the chronically ill, immunodeficient patients, and people travelling abroad. The compositions are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 12 weeks, about 16 weeks, etc.).

Compositions of the invention may be administered to patients at substantially the same time as (e.g. during the same medical consultation or visit to a healthcare professional) other compositions, and in particular at the same time as other vaccines.

Immunogenic compositions comprise an immunologically effective amount of saccharide antigen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses).

Vaccines according to the invention may either be prophylactic (i.e. to prevent infection) or therapeutic (i.e. to treat disease after infection), but will typically be prophylactic.

Adjuvants

Compositions of the invention may advantageously include an adjuvant, which can function to enhance the immune responses elicited in a patient who receives the composition. Adjuvants that can be used with the invention include, but are not limited to:

A mineral-containing composition, including calcium salts and aluminum salts (or mixtures thereof). Calcium salts include calcium phosphate (e.g. the "CAP" particles disclosed in ref. 53). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [54]. Aluminum salt adjuvants are described in more detail below.

An oil-in-water emulsion, as described in more detail below.

An immunostimulatory oligonucleotide, such as one containing a CpG motif (a dinucleotide sequence containing an unmethylated cytosine linked by a phosphate bond to a guanosine), a TpG motif [55], a double-stranded RNA, an oligonucleotide containing a palindromic sequence; or an oligonucleotide containing a poly(dG) sequence. Immunostimulatory oligonucleotides can include nucleotide modifications/analogs such as phosphorothioate modifications and can be double-stranded or (except for RNA) single-stranded. References 56 to 58 disclose possible analog substitutions e.g. replacement of guanosine with 2'-deoxy-7-deazaguanosine. The adjuvant effect of CpG oligonucleotides is further discussed in refs. 59-64. A CpG sequence may be directed to TLR9, such as the motif GTCGTT or TTCGTT [65]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 66-68. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 65 & 69-71. A useful CpG adjuvant is CpG7909, also known as ProMune™ (Coley Pharmaceutical Group, Inc.). Immunostimulatory oligonucleotides will typically comprise at least 20 nucleotides. They may comprise fewer than 100 nucleotides.

3-O-deacylated monophosphoryl lipid A ('3dMPL', also known as 'MPL™') [72-75]. 3dMPL has been prepared from a heptoseless mutant of *Salmonella minnesota*, and is chemically similar to lipid A but lacks an acid-labile phosphoryl group and a base-labile acyl group. Preparation of 3dMPL was originally described in reference 76. 3dMPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position.

An imidazoquinoline compound, such as Imiquimod ("R-837") [77,78], Resiquimod ("R-848") [79], and their analogs; and salts thereof (e.g. the hydrochloride salts). Further details about immunostimulatory imidazoquinolines can be found in references 80 to 84.

A thiosemicarbazone compound, such as those disclosed in reference 85. Methods of formulating, manufacturing, and screening for active compounds are also described in reference 85. The thiosemicarbazones are particularly effective in the stimulation of human peripheral blood mononuclear cells for the production of cytokines, such as TNF-α.

A tryptanthrin compound, such as those disclosed in reference 86. Methods of formulating, manufacturing, and screening for active compounds are also described in reference 86. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

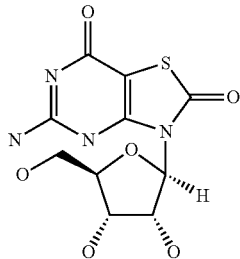 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 87 to 89; (f) a compound having the formula:

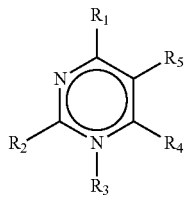

wherein:
- $R_1$ and $R_2$ are each independently H, halo, $-NR_aR_b$, $-OH$, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;
- $R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;
- $R_4$ and $R_5$ are each independently H, halo, heterocyclyl, substituted heterocyclyl, $-C(O)-R_d$, $C_{1-6}$ alkyl, substituted $C_{1-6}$ alkyl, or bound together to form a 5 membered ring as in $R_{4-5}$:

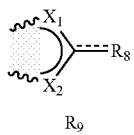

the binding being achieved at the bonds indicated by a ⌇
- $X_1$ and $X_2$ are each independently N, C, O, or S;
- $R_8$ is H, halo, $-OH$, $C_{1-6}$ alkyl, $C_{2-6}$ alkenyl, $C_{2-6}$ alkynyl, $-OH$, $-NR_aR_b$, $-(CH_2)_n-O-R_c$, $-O-(C_{1-6}$ alkyl), $-S(O)_pR_e$, or $-C(O)-R_d$;
- $R_9$ is H, $C_{1-6}$ alkyl, substituted $C_{1-6}$ alkyl, heterocyclyl, substituted heterocyclyl or $R_{9a}$, wherein $R_{9a}$ is:

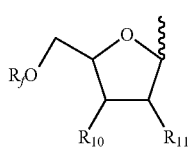

the binding being achieved at the bond indicated by a ⌇
- $R_{10}$ and $R_{11}$ are each independently H, halo, $C_{1-6}$ alkoxy, substituted $C_{1-6}$ alkoxy, $-NR_aR_b$, or $-OH$;
- each $R_a$ and $R_b$ is independently H, $C_{1-6}$ alkyl, substituted $C_{1-6}$ alkyl, $-C(O)R_d$, $C_{6-10}$ aryl;
- each $R_c$ is independently H, phosphate, diphosphate, triphosphate, $C_{1-6}$ alkyl, or substituted $C_{1-6}$ alkyl;
- each $R_d$ is independently H, halo, $C_{1-6}$ alkyl, substituted $C_{1-6}$ alkyl, $C_{1-6}$ alkoxy, substituted $C_{1-6}$ alkoxy, $-NH_2$, $-NH(C_{1-6}$ alkyl), $-NH(\text{substituted } C_{1-6}$ alkyl), $-N(C_{1-6}$ alkyl)$_2$, $-N(\text{substituted } C_{1-6}$ alkyl)$_2$, $C_{6-10}$ aryl, or heterocyclyl;
- each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;
- each $R_f$ is independently H, $C_{1-6}$ alkyl, substituted $C_{1-6}$ alkyl, $-C(O)R_d$, phosphate, diphosphate, or triphosphate;
- each n is independently 0, 1, 2, or 3;
- each p is independently 0, 1, or 2; or or (g) a pharmaceutically acceptable salt of any of (a) to (f), a tautomer of any of (a) to (f), or a pharmaceutically acceptable salt of the tautomer.

Loxoribine (7-allyl-8-oxoguanosine) [90].

Compounds disclosed in reference 91, including: Acylpiperazine compounds, Indoledione compounds, Tetrahydroisoquinoline (THIQ) compounds, Benzocyclodione compounds, Aminoazavinyl compounds, Aminobenzimidazole quinolinone (ABIQ) compounds [92,93], Hydrapthalamide compounds, Benzophenone compounds, Isoxazole compounds, Sterol compounds, Quinazilinone compounds, Pyrrole compounds [94], Anthraquinone compounds, Quinoxaline compounds, Triazine compounds, Pyrazalopyrimidine compounds, and Benzazole compounds [95].

Compounds disclosed in reference 96, including 3,4-di(1H-indol-3-yl)-1H-pyrrole-2,5-diones, staurosporine analogs, derivatized pyridazines, chromen-4-ones, indolinones, quinazolines, and nucleoside analogs.

An aminoalkyl glucosaminide phosphate derivative, such as RC-529 [97,98].

A phosphazene, such as poly[di(carboxylatophenoxy)phosphazene] ("PCPP") as described, for example, in references 99 and 100.

Small molecule immunopotentiators (SMIPs) such as:
N2-methyl-1-(2-methylpropyl)-1H-imidazo[4,5-c]quinoline-2,4-diamine
N2,N2-dimethyl-1-(2-methylpropyl)-1H-imidazo[4,5-c]quinoline-2,4-diamine
N2-ethyl-N2-methyl-1-(2-methylpropyl)-1H-imidazo[4,5-c]quinoline-2,4-diamine
N2-methyl-1-(2-methylpropyl)-N2-propyl-1H-imidazo[4,5-c]quinoline-2,4-diamine
1-(2-methylpropyl)-N2-propyl-1H-imidazo[4,5-c]quinoline-2,4-diamine
N2-butyl-1-(2-methylpropyl)-1H-imidazo[4,5-c]quinoline-2,4-diamine
N2-butyl-N2-methyl-1-(2-methylpropyl)-1H-imidazo[4,5-c]quinoline-2,4-diamine
N2-methyl-1-(2-methylpropyl)-N2-pentyl-1H-imidazo[4,5-c]quinoline-2,4-diamine
N2-methyl-1-(2-methylpropyl)-N2-prop-2-enyl-1H-imidazo[4,5-c]quinoline-2,4-diamine
1-(2-methylpropyl)-2-[(phenylmethyl)thio]-1H-imidazo[4,5-c]quinolin-4-amine 1-(2-methylpropyl)-2-(propylthio)-1H-imidazo[4,5-c]qui-
nolin-4-amine
2-[[4-amino-1-(2-methylpropyl)-1H-imidazo[4,5-c]quino-
lin-2-yl](methyl)amino]ethanol
2-[[4-amino-1-(2-methylpropyl)-1H-imidazo[4,5-c]quino-
lin-2-yl](methyl)amino]ethyl acetate
4-amino-1-(2-methylpropyl)-1,3-dihydro-2H-imidazo[4,5-
c]quinolin-2-one
N2-butyl-1-(2-methylpropyl)-N4,N4-bis(phenylmethyl)-
1H-imidazo[4,5-c]quinoline-2,4-diamine
N2-butyl-N2-methyl-1-(2-methylpropyl)-N4,N4-bis(phe-
nylmethyl)-1H-imidazo[4,5-c]quinoline-2,4-diamine
N2-methyl-1-(2-methylpropyl)-N4,N4-bis(phenylmethyl)-
1H-imidazo[4,5-c]quinoline-2,4-diamine
N2,N2-dimethyl-1-(2-methylpropyl)-N4,N4-bis(phenylm-
ethyl)-1H-imidazo[4,5-c]quinoline-2,4-diamine
1-{4-amino-2-[methyl(propyl)amino]-1H-imidazo[4,5-c]
quinolin-1-yl}-2-methylpropan-2-ol
1-[4-amino-2-(propylamino)-1H-imidazo[4,5-c]quinolin-1-
yl]-2-methylpropan-2-ol
N4,N4-dibenzyl-1-(2-methoxy-2-methylpropyl)-N2-pro-
pyl-1H-imidazo[4,5-c]quinoline-2,4-diamine.

Saponins [chapter 22 of ref. 131], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 101. Saponin formulations may also comprise a sterol, such as cholesterol [102]. Combinations of saponins and cholesterols can be used to form unique particles called immunostimulating complexes (ISCOMs) [chapter 23 of ref 131]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 102-104. Optionally, the ISCOMS may be devoid of additional detergent [105]. A review of the development of saponin based adjuvants can be found in refs. 106 & 107.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [108]. The use of detoxified ADP-ribosylating toxins as mucosal adjuvants is described in ref. 109 and as parenteral adjuvants in ref. 110.

Bioadhesives and mucoadhesives, such as esterified hyaluronic acid microspheres [111] or chitosan and its derivatives [112].

Microparticles (i.e. a particle of ~100 nm to ~150 µm in diameter, more preferably ~200 nm to ~30 µm in diameter, or ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref. 131). Examples of liposome formulations suitable for use as adjuvants are described in refs. 113-115.

Polyoxyethylene ethers and polyoxyethylene esters [116]. Such formulations further include polyoxyethylene sorbitan ester surfactants in combination with an octoxynol [117] as well as polyoxyethylene alkyl ethers or ester surfactants in combination with at least one additional non-ionic surfactant such as an octoxynol [118]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide (LPS) preparation derived from a second Gram-negative bacterium, wherein the outer membrane protein proteosome and LPS preparations form a stable non-covalent adjuvant complex. Such complexes include "IVX-908", a complex comprised of *Neisseria meningitidis* outer membrane and LPS.

Methyl inosine 5'-monophosphate ("MIMP") [119].

A polyhydroxlated pyrrolizidine compound [120], such as one having formula:

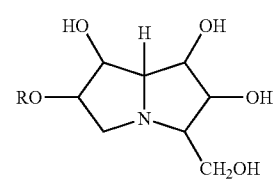

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A gamma inulin [121] or derivative thereof, such as algammulin.

A compound of formula I, II or III, or a salt thereof:

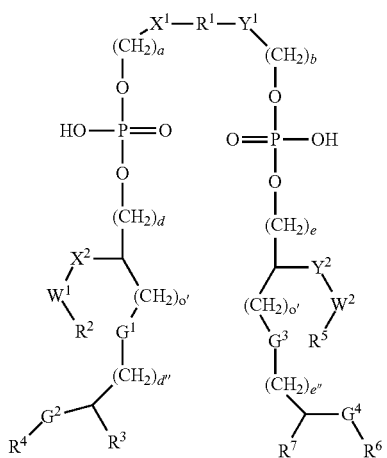

I

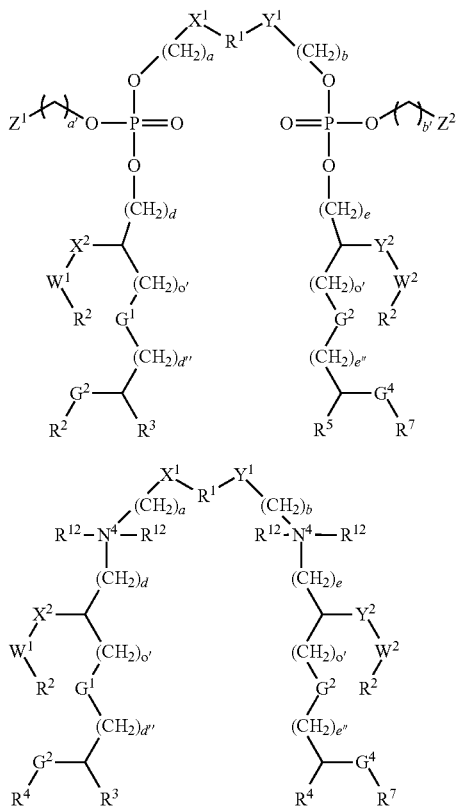

II

III as defined in reference 122, such as 'ER 803058', 'ER 803732', 'ER 804053', ER 804058', 'ER 804059', 'ER 804442', 'ER 804680', 'ER 804764', ER 803022 or 'ER 804057' e.g.:

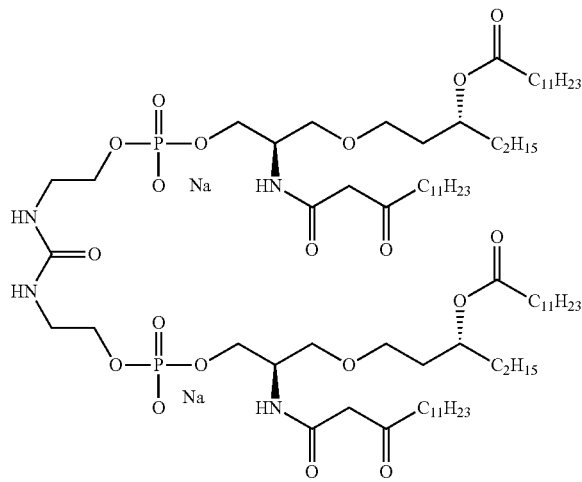

ER804057

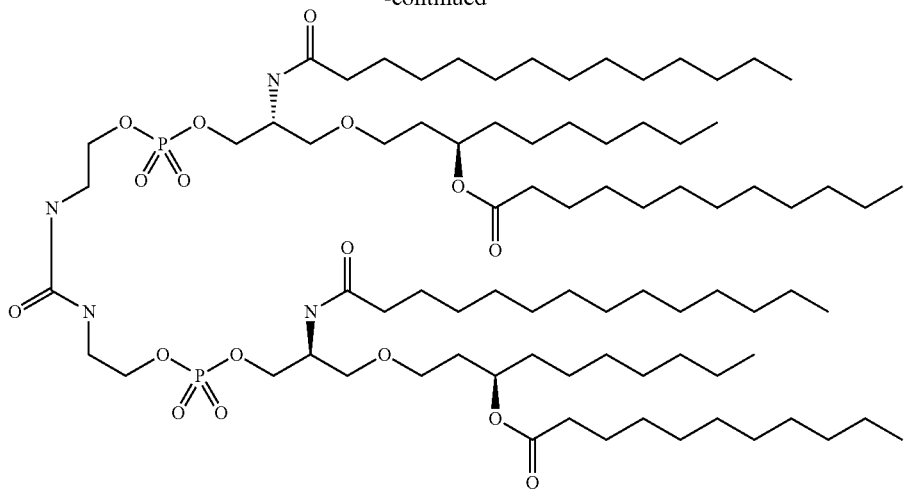

ER-803022:

Derivatives of lipid A from *Escherichia coli* such as OM-174 (described in refs. 123 & 124).

A formulation of a cationic lipid and a (usually neutral) co-lipid, such as aminopropyl-dimethyl-myristoley-loxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred [125], Compounds containing lipids linked to a phosphate-containing acyclic backbone, such as the TLR4 antagonist E5564 [126,127]:

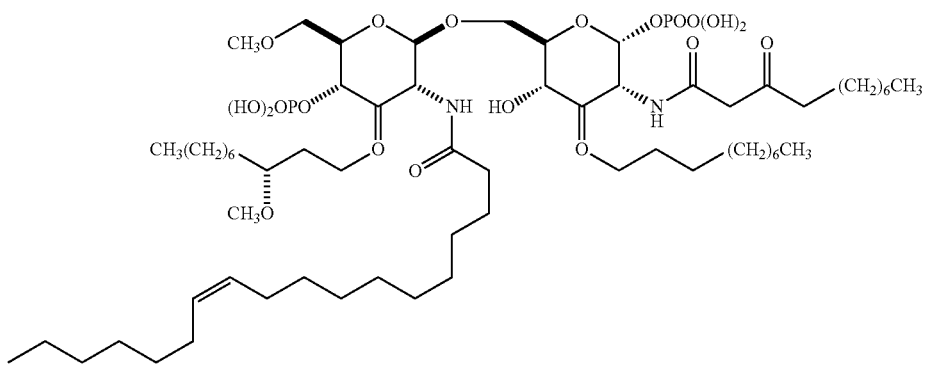

These and other adjuvant-active substances are discussed in more detail in references 131 & 132. Compositions may include two or more of said adjuvants.

Antigens and adjuvants in a composition will typically be in admixture.

Oil-in-Water Emulsion Adjuvants

Oil-in-water emulsions are particularly useful as adjuvants. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate), Span 85 (sorbitan trioleate), lecithin and Triton X-100. Mixtures of surfactants can be used e.g. Tween 80/Span 85 mixtures.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [128-130], as described in more detail in Chapter 10 of ref. 131 and chapter 12 of ref. 132. The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100).
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [133] (0.05-1% Thr-MDP, 5% squalane, 2.5% Pluronic L121 and 0.2% polysorbate 80). It can also be used without the Thr-MDP, as in the "AF" adjuvant [134] (5% squalane, 1.25% Pluronic L121 and 0.2% polysorbate 80). Microfluidisation is preferred.
- An emulsion having from 0.5-50% of an oil, 0.1-10% of a phospholipid, and 0.05-5% of a non-ionic surfactant. As described in reference 135, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 136, produced by addition of aliphatic amine to desacylsaponin via the carboxyl group of glucuronic acid), dimethyldioctadecylammonium bromide and/or N,N-dioctadecyl-N, N-bis(2-hydroxyethyl)propanediamine.
- An emulsion in which a saponin (e.g. QuilA or QS21) and a sterol (e.g. a cholesterol) are associated as helical micelles [137].

The emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

Aluminum Salt Adjuvants

The adjuvants known as aluminum hydroxide and aluminum phosphate may be used. These names are conventional, but are used for convenience only, as neither is a precise description of the actual chemical compound which is present (e.g. see chapter 9 of reference 131). The invention can use any of the "hydroxide" or "phosphate" adjuvants that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 131]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++\ at\ pH}$ 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls [ch. 9 of ref 131]

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included, at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate is associated with a more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml.

Further Antigens

As well as modified saccharides and/or conjugates, the composition may comprise further antigenic components. For instance, the composition may include one or more further saccharides (whether or not modified according to the invention). For instance, the composition may comprise saccharides from serogroups C, W135 and Y of *N. meningitidis* (e.g. in addition to a modified MenA saccharide). These will typically be conjugated to carrier proteins, and saccharides from different serogroups of *N. meningitidis* may be conjugated to the same or different carrier proteins. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Improved immunogenicity of the MenA component has been observed when it is present in excess (mass/dose) to the MenC component [138].

The composition may also comprise protein antigens.

Antigens which can be included in the composition of the invention include:
- a protein antigen from *N. meningitidis* serogroup B (see below).
- an outer-membrane vesicle (OMV) preparation from *N. meningitidis*, such as those disclosed in refs. 139, 140, 141, 142 etc.
- antigens from *Helicobacter pylori* such as CagA [143 to 146], VacA [147, 148], NAP [149, 150, 151], HopX [e.g. 152], HopY [e.g. 152] and/or urease.
- a saccharide antigen from *Streptococcus pneumoniae* [e.g. 153, 154, 155].
- an antigen from hepatitis A virus, such as inactivated virus [e.g. 156, 157].
- an antigen from hepatitis B virus, such as the surface and/or core antigens [e.g. 157, 158].
- an antigen from hepatitis C virus [e.g. 159].
- an acellular antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 160 & 161].
- a cellular *Bordetella pertussis* antigen.
- a diphtheria antigen, such as a diphtheria toxoid [e.g. chapter 3 of ref. 162] e.g. the $CRM_{197}$ mutant [e.g. 163].
- polio antigen(s) [e.g. 164, 165] such as inactivated polio virus (IPV)
- a tetanus antigen, such as a tetanus toxoid [e.g. chapter 4 of ref. 162].
- a saccharide antigen from *Haemophilus influenzae* B [e.g. refs. 166 to 174].
- measles, mumps and/or rubella antigens [e.g. chapters 9, 10 & 11 of ref. 162].
- an antigen from *N. gonorrhoeae*.
- an antigen from *Chlamydia pneumoniae* [e.g. 175, 176, 177, 178, 179, 180, 181].
- an antigen from *Chlamydia trachomatis* [e.g. 182].
- an antigen from *Porphyromonas gingivalis* [e.g. 183].
- rabies antigen(s) [e.g. 184] such as lyophilised inactivated virus [e.g. 185, RabAvert™].
- influenza antigen(s) [e.g. chapter 19 of ref. 162], such as the haemagglutinin and/or neuraminidase surface proteins.
- an antigen from *Moraxella catarrhalis* [e.g. 186].
- an antigen from *Streptococcus agalactiae* (group B *streptococcus*) [e.g. 187, 188].
- a saccharide antigen from *Streptococcus agalactiae* (group B *streptococcus*).
- an antigen from *Streptococcus pyogenes* (group A *streptococcus*) [e.g. 188, 189, 190].
- an antigen from *Staphylococcus aureus* [e.g. 191].
- an antigen from *Bacillus anthracis* [e.g. 192, 193, 194].
- a herpes simplex virus (HSV) antigen. A preferred HSV antigen for use with the invention is membrane glycoprotein gD. It is preferred to use gD from a HSV-2 strain ('gD2' antigen). The composition can use a form of gD in which the C-terminal membrane anchor region has been deleted [195] e.g. a truncated gD comprising amino acids 1-306 of the natural protein with the addition of aparagine and glutamine at the C-terminus. This form of the protein includes the signal peptide which is cleaved to yield a mature 283 amino acid protein. Deletion of the anchor allows the protein to be prepared in soluble form.

- a human papillomavirus (HPV) antigen. Preferred HPV antigens for use with the invention are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [196]. In addition to HPV-16 and HPV-18 strains, it is also possible to include L1 VLPs from HPV-6 and HPV-11 strains. The use of oncogenic HPV strains is also possible. A vaccine may include between 20-60 µg/ml (e.g. about 40 µg/ml) of L1 per HPV strain.
- an antigen from a virus in the flaviviridae family (genus *flavivirus*), such as from yellow fever virus, Japanese encephalitis virus, four serotypes of Dengue viruses, tick-borne encephalitis virus, West Nile virus.
- a pestivirus antigen, such as from classical porcine fever virus, bovine viral diarrhoea virus, and/or border disease virus.
- a parvovirus antigen e.g. from parvovirus B19.
- a prion protein (e.g. the CJD prion protein)
- an amyloid protein, such as a beta peptide [197]
- a cancer antigen, such as those listed in Table 1 of ref. 198 or in tables 3 & 4 of ref. 199.

The composition may comprise one or more of these further antigens.

Toxic protein antigens may be detoxified where necessary (e.g. detoxification of pertussis toxin by chemical and/or genetic means [161]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens may be adsorbed to an aluminium salt.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 200 to 208]. Protein components of the compositions of the invention may thus be replaced by nucleic acid (preferably DNA e.g. in the form of a plasmid) that encodes the protein.

Non-Saccharide Meningococcal Antigens

Although the capsular saccharides of meningococcal serogroups A, C, W135 and Y can be used to generate protective immunity, the same approach hag not worked for serogroup B. Thus the modified saccharides and conjugates of the invention can be used together (e.g. separately or in admixture) with meningococcal antigens that are not based on capsular saccharides e.g. protein antigens, lipopolysaccharides, or membrane vesicles.

Genome sequences for meningococcal serogroups A [209] and B [210,211] have been reported, and suitable protein antigens can be selected from the encoded polypeptides [e.g. refs. 212-217]. Candidate antigens have been manipulated to improve heterologous expression [refs. 218 to 220].

One preferred composition includes a Tbp protein and a Hsf protein [221]. Hsf is an autotransporter protein [222-224], also known as nhhA [224], GNA0992 [212] or NMB0992 [210]. Tbp is the transferrin binding protein [225-228], and encompasses both TbpA and TbpB and the high molecular weight and low molecular weight forms of TbpA and TbpB. Tbp encompasses individual proteins described above and complexes of the proteins and any other proteins or complexes thereof capable of binding transferrin. Although Tbp can refer to either the high or low molecular forms of TbpA or TbpB, it is preferred that both high molecular weight and low molecular weight forms of TbpA and/or TbpB are present. Most preferably, high molecular weight and low molecular weight TbpA is present.

Another preferred composition includes at least one antigen selected from each of at least two different categories of protein having different functions within *Neisseria*. Examples of such categories of proteins are: adhesins, autotransporter proteins, toxins, integral outer membrane proteins and iron acquisition proteins. These antigens may be selected as follows, using the nomenclature of reference 229: at least one Neisserial adhesin selected from the group consisting of FhaB, NspA PilC, Hsf, Hap, MafA, MafB, Omp26, NMB0315, NMB0995, NMB1119 and NadA; at least one Neisserial autotransporter selected from the group consisting of Hsf; Hap; IgA protease, AspA, and NadA; at least one Neisserial toxin selected from the group consisting of FrpA, FrpC, FrpA/C, VapD, NM-ADPRT (NMB1343) and either or both of LPS immunotype L2 and LPS immunotype L3; at least one Neisserial Fe acquisition protein selected from the group consisting of TbpA, TbpB, LbpA, LbpB, HpuA, HpuB, Lipo28 (GNA2132), Sibp, NMB0964, NMB0293, FbpA, Bcp, BfrA, BfrB and P2086 (XthA); at least one Neisserial membrane-associated protein, preferably outer membrane protein, particularly integral outer membrane protein, selected from the group consisting of PilQ, OMP85, FhaC, NspA, TbpA, LbpA, TspA, TspB, TdfH, PorB, MltA, HpuB, HimD, HisD, GNA1870, OstA, HlpA (GNA1946), NMB1124, NMB1162, NMB1220, NMB1313, NMB1953, HtrA, and PLDA (OMPLA). These combinations of Neisserial antigens are said to lead to a surprising enhancement of the efficacy of the vaccine against Neisserial infection [229].

Particularly preferred compositions include one or more of the following five antigens [230]: (1) a 'NadA' protein, preferably in oligomeric form (e.g. in trimeric form); (2) a '741' protein; (3) a '936' protein; (4) a '953' protein; and (5) a '287' protein.

'NadA' (Neisserial adhesin A) from MenB is disclosed as protein '961' in reference 215 (SEQ IDs 2943 & 2944) and as 'NMB1994' in reference 210 (see also GenBank accession GI: 11352904 & 7227256). A detailed study of the protein can be found in reference 231. When used according to the present invention, NadA may take various forms. Preferred forms of NadA are truncation or deletion variants of the wild-type sequence, such as those disclosed in references 218 to 220. In particular, NadA without its C-terminal membrane anchor is preferred (e.g. deletion of residues 351-405 for the 2996 strain).

'741' protein from MenB is disclosed in reference 215 (SEQ IDs 2535 & 2536) and as 'NMB1870' in reference 210 (see also GenBank accession number GI:7227128). The corresponding protein in serogroup A [209] has GenBank accession number 7379322. 741 is naturally a lipoprotein. When used according to the present invention, 741 protein may take various forms. Preferred forms of 741 are truncation or deletion variants of the wild-type sequence, such as those disclosed in references 218 to 220. In particular, the N-terminus of 741 may be deleted up to and including its poly-glycine sequence (i.e. deletion of residues 1 to 72 for strain MC58), which may sometimes be distinguished herein by the use of a 'ΔG' prefix. This deletion can enhance expression. The deletion also removes 741's lipidation site. Various 741 sequences can be found in SEQ IDs 1 to 22 of reference 220, in SEQ IDs 1 to 23 of reference 232, and in SEQ IDs 1-299 of reference 233.

'936' protein from serogroup B is disclosed in reference 215 (SEQ IDs 2883 & 2884) and as 'NMB2091' in reference 210 (see also GenBank accession number GI:7227353). The corresponding gene in serogroup A [209] has GenBank accession number 7379093. When used according to the present invention, 936 protein may take various forms. Preferred forms of 936 are truncation or deletion variants of the wild-type sequence, such as those disclosed in references 218 to 220. In particular, the N-terminus leader peptide of 936 may be deleted (e.g. deletion of residues 1 to 23 for strain MC58, to give $936^{(NL)}$).

'953' protein from serogroup B is disclosed in reference 215 (SEQ IDs 2917 & 2918) and as 'NMB1030' in reference 210 (see also GenBank accession number GI:7226269). The corresponding protein in serogroup A [209] has GenBank accession number 7380108. When used according to the present invention, 953 protein may take various forms. Preferred forms of 953 are truncation or deletion variants of the wild-type sequence, such as those disclosed in references 218 to 220. In particular, the N-terminus leader peptide of 953 may be deleted (e.g. deletion of residues 1 to 19 for strain MC58).

'287' protein from serogroup B is disclosed in reference 215 (SEQ IDs 3103.& 3104), as 'NMB2132' in reference 210, and as 'GNA2132' in reference 212 (see also GenBank accession number GI:7227388). The corresponding protein in serogroup A [209] has GenBank accession number 7379057. When used according to the present invention, 287 protein may take various forms. Preferred forms of 287 are truncation or deletion variants of the wild-type sequence, such as those disclosed in references 218 to 220. In particular, the N-terminus of 287 may be deleted up to and including its poly-glycine sequence (e.g. deletion of residues 1 to 24 for strain MC58, to give ΔG287).

Protein 287 is preferably from strain 2996 or, more preferably, from strain 394/98. Protein 741 is preferably from serogroup B strains MC58, 2996, 394/98, or 95N477, or from serogroup C strain 90/18311. Strain MC58 is more preferred. Proteins 936, 953 and NadA are preferably from strain 2996. Where a composition includes a particular protein antigen (e.g. 741 or 287), the composition can include that antigen in more than one variant form e.g. the same protein, but from more than one strain. These proteins may be included as tandem or separate proteins.

Other MenB polypeptide antigens which may be included in compositions of the invention include those comprising one of the following amino acid sequences: SEQ ID NO:650 from ref. 213; SEQ ID NO:878 from ref. 213; SEQ ID NO:884 from ref. 213; SEQ ID NO:4 from ref. 214; SEQ ID NO:598 from ref. 215; SEQ ID NO:818 from ref. 215; SEQ ID NO:864 from ref. 215; SEQ ID NO:866 from ref. 215; SEQ ID NO:1196 from ref. 215; SEQ ID NO:1272 from ref. 215; SEQ ID NO:1274 from ref. 215; SEQ ID NO:1640 from ref. 215; SEQ ID NO:1788 from ref. 215; SEQ ID NO:2288 from ref. 215; SEQ ID NO:2466 from ref. 215; SEQ ID NO:2554 from ref. 215; SEQ ID NO:2576 from ref. 215; SEQ ID NO:2606 from ref. 215; SEQ ID NO:2608 from ref. 215; SEQ ID NO:2616 from ref. 215; SEQ ID NO:2668 from ref. 215; SEQ ID NO:2780 from ref. 215; SEQ ID NO:2932 from ref. 215; SEQ ID NO:2958 from ref. 215; SEQ ID NO:2970 from ref. 215; SEQ ID NO:2988 from ref. 215, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6, 7, 8, 9, 10, 11, 12, 13, 14 or more) of these polypeptides may be included.

In some embodiments, however, the composition of the invention includes the same protein but from more than one strain. This approach has been found to be effective with the 741 protein. This protein is an extremely effective antigen for eliciting anti-meningococcal antibody responses, and it is expressed across all meningococcal serogroups. Phylogenetic analysis shows that the protein splits into two groups, and that one of these splits again to give three variants in total [234], and while serum raised against a given variant is bactericidal within the same variant group, it is not active against strains which express one of the other two variants i.e. there is intra-variant cross-protection, but not inter-variant cross-protection [232,234]. For maximum cross-strain efficacy, therefore, it is preferred that a composition should include more than one variant of protein 741.

Compositions of the invention include a small number (e.g. fewer than t antigens, where t is 10, 9, 8, 7, 6, 5, 4 or 3) of purified serogroup B proteins. The proteins are preferably expressed recombinantly in a heterologous host and then purified. For a composition including t MenB antigens, there may be t separate polypeptides but, to reduce complexity even further, it is preferred that at least two of the antigens are expressed as a single polypeptide chain (a 'hybrid' protein [refs. 218 to 220]) i.e. such that the t antigens form fewer than t polypeptides. Hybrid proteins offer two principal advantages: first, a protein that may be unstable or poorly expressed on its own can be assisted by adding a suitable hybrid partner that overcomes the problem; second, commercial manufacture is simplified as only one expression and purification need be employed in order to produce two separately-useful proteins. A hybrid included in a composition of the invention may comprise two or more (i.e. 2, 3, 4 or 5) of the five proteins listed above. Hybrids consisting of two of the five proteins are preferred.

Another preferred composition includes serogroup B lipooligosaccharide (LOS) [235]. LOS can be used in addition to the serogroup B polypeptide(s) or can be used in place of it/them.

Membrane vesicles may also be used in the compositions. These vesicles can be any proteoliposomic vesicle obtained by disrupting a meningococcal outer membrane to form vesicles of the outer membrane which include protein components of the outer membrane. 'OMVs' are prepared artificially from bacteria (e.g. by detergent treatment) and are thus distinct from microvesicles (MVs [236]) and 'native OMVs' ('NOMVs' [237]), both of which are naturally-occurring membrane vesicles that form spontaneously during bacterial growth and are released into culture medium. MVs can be obtained by culturing *Neisseria* in broth culture medium, separating whole cells from the smaller blebs in the broth culture medium, and then collecting the MVs from the cell-depleted medium. Strains for use in production of MVs can generally be selected on the basis of the amount of MVs produced in culture e.g. refs. 238 & 239 describe *Neisseria* with high MV production. Vesicles can also be obtained from mltA knockout strains [240].

To reduce pyrogenic activity, it is preferred that the bacterium should have low endotoxin (LPS) levels. Suitable mutant bacteria are known e.g. mutant *Neisseria* [241] and mutant *Helicobacter* [242]. Processes for preparing LPS-depleted outer membranes from Gram-negative bacteria are disclosed in reference 243.

The bacterium may be a wild-type bacterium, or it may be a recombinant bacterium. Preferred recombinant bacteria over-express (relative to the corresponding wild-type strain) immunogens such as NspA, protein 287 [244], protein 741 [244], TbpA, TbpB, superoxide dismutase [245], etc. The bacterium may express more than one PorA class I outer membrane protein e.g. 2, 3, 4, 5 or 6 of PorA subtypes: P1.7,16; P1.5,2; P1.19,15; P1.5c, 10; P1.12,13; and P1.7h,4 [e.g. refs. 246 & 247].

Other recombinant bacteria that can be used with the invention have one or more mutations to decrease (or, preferably, to knockout) expression of particular gene products (e.g. see refs 248 & 249). Preferred genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorA, PorB, SiaA, SiaB, SiaC, SiaD, TbpA, and/or TbpB [248]; (b) CtrA, CtrB, CtrC, CtrD, FrpB, GalE, HtrB/MsbB, LbpA, LbpB, LpxK, Opa, Opc, PhoP, PilC, PmrE, PmrF, PorA, SiaA, SiaB, SiaC, SiaD, TbpA, and/or TbpB [249]; (c) lytic transglycosylase NMB0033 [250]; (d) ExbB, ExbD, rmpM, CtrA, CtrB, CtrD, GalE, LbpA, LpbB, Opa, Opc, PilC, PorA, PorB, SiaA, SiaB, SiaC, SiaD, TbpA, and/or TbpB [251]; and (e) CtrA, CtrB, CtrD, FrpB, OpA, OpC, PilA, PorA, PorB, SiaD, SynA, SynB, and/or SynC [252].

Preferred strains within serogroup B as the source for these non-saccharide antigens are MC58, 2996, H44/76, 394/98 and New Zealand strain 98/254. The best serotypes and strains to use, however, will depend on the strains prevalent in a particular geographical location. For example, the meningococcus can be of any serotype (e.g. 1, 2a, 2b, 4, 14, 15, 16, etc.), of any serosubtype (P1.2; P1.4; P1.5; P1.5,2; P1.7,16; P1.7,16b; P1.9; P1.9,15; P1.12,13; P1.13; P1.14; P1.15; P1.21,16; P1.22,14; etc.) and of any immunotype (e.g. L1; L3,3,7; L10; etc.), and preferred strains include: (a) B:4:P1.4; (b) B:4:P1.15; (c) B:15:P1.7,16; and (d) B:4:P1.7b,4. The meningococcus may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 253] e.g. the ET-37 complex is the ST-11 complex by MLST, the ET-5 complex is ST-32 (ET-5), lineage 3 is ST-41/44, etc.

Non-saccharide antigens can be used to induce a serum bactericidal antibody response that is effective against two or three of MenB hypervirulent lineages A4, ET-5 and lineage 3. They may additionally induce bactericidal antibody responses against one or more of hypervirulent lineages subgroup I, subgroup III, subgroup IV-1 or ET-37 complex, and against other lineages e.g. hyperinvasive lineages. These antibody responses are conveniently measured in mice and are a standard indicator of vaccine efficacy [e.g. see end-note 14 of reference 212]. Serum bactericidal activity (SBA) measures bacterial killing mediated by complement, and can be assayed using human or baby rabbit complement. WHO standards require a vaccine to induce at least a 4-fold rise in SBA in more than 90% of recipients.

The composition need not induce bactericidal antibodies against each and every MenB strain within these hypervirulent lineages; rather, for any given group of four of more strains of serogroup B meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1/1024, as described in reference 212.

Preferred compositions can induce bactericidal responses against the following strains of serogroup B meningococcus: (i) from cluster A4, strain 961-5945 (B:2b:P1.21,16) and/or strain G2136 (B:-); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:-). More preferred compositions can induce bactericidal responses against strains 961-5945, 44/76 and 394/98. Strains 961-5945 and G2136 are both *Neisseria* MLST reference strains [ids 638 & 1002 in ref. 254]. Strain MC58 is widely available (e.g. ATCC BAA-335) and was the strain sequenced in reference 210. Strain 44/76 has been widely used and characterised (e.g. ref. 255) and is one of the *Neisseria* MLST reference strains [id 237 in ref. 254; row 32 of Table 2 in ref. 256]. Strain 394/98 was originally isolated in New Zealand in 1998, and there have been several published studies using this strain (e.g. refs. 257 & 258). Strain BZ198 is another MLST reference strain [id 409 in ref. 254; row 41 of Table 2 in ref. 256]. The composition may additionally induce a bactericidal response against serogroup W135 strain LNP17592 (W135:2a:P1.5,2), from ET-37 complex.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The term "alkyl" is used herein to refer to alkyl groups in both straight and branched forms. However, the term "alkyl" usually refers to alkyl groups in straight forms. The alkyl group may be interrupted with 1, 2 or 3 heteroatoms selected from —O—, —NH— or —S—. The alkyl group may also be interrupted with 1, 2 or 3 double and/or triple bonds; However, the term "alkyl" usually refers to alkyl groups having no heteroatom interruptions or double or triple bond interruptions. Where reference is made to $C_{1-6}$ alkyl, it is meant the alkyl group may contain any number of carbon atoms between 1 and 6 (e.g. $C_1$, $C_2$, $C_3$, $C_4$, $C_5/C_6$).

The term "alkylene" is used herein to refer to a divalent alkyl group, as defined above. Where reference is made to $C_{1-5}$ alkylene, it is meant the alkylene group may contain any number of carbon atoms between 1 and 5 (e.g. $C_1$, $C_2$, $C_3$, $C_4$, $C_5$). Similarly, where reference is made to $C_{1-4}$ alkylene, it is meant the alkylene group may contain any number of carbon atoms between 1 and 4 (e.g. $C_1$, $C_3$, $C_4$).

The term "amino group" includes groups of the formula —$NH_2$ or —NH-E, where E is a nitrogen protecting group. Examples of typical nitrogen protecting groups are described above.

The term "amine" means a group of the formula —$NH_2$, unless the context indicates otherwise.

The term "modified capsular saccharide" means a saccharide that is obtainable from a native capsular saccharide by suitable modification. Hence, the basic sequence of repeating monosaccharide units in the native capsular saccharide is retained in the modified capsular saccharides of the present invention.

The term "saccharide" encompasses both oligosaccharides (e.g. containing from 2 to 39 monosaccharide units) and polysaccharides (e.g. containing 40 or more monosaccharide units). As found naturally in bacteria, native capsular saccharides generally take the form of polysaccharides. Polysaccharides may be manipulated to give shorter oligosaccharides. Oligosaccharides may be obtained by purification and/or depolymerising followed by sizing of the native polysaccharide (e.g. by hydrolysis in mild acid, by heating, by sizing chromatography etc.).

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

It will be appreciated that ionisable groups may exist in the neutral form shown in formulae herein, or may exist in charged form e.g. depending on pH. Thus a phosphate group may be shown as —P—O—$(OH)_2$, this formula is merely representative of the neutral phosphate group, and other charged forms are encompassed by the invention. Similarly, references herein to cationic and anionic groups should be taken to refer to the charge that is present on that group under physiological conditions e.g. where an amine —$NH_2$ is protonated to give the cationic —$NH^{3+}$ group, this protonation is one that occurs at physiological pH. In addition where a carboxyl —COOH is deprotonated to give the anionic —$COO^-$ group, this protonation is one that can occur at physiological pH. Moreover, the invention encompasses salts of the charged forms of molecules of the invention. Sugar rings can exist in open and closed form and, while closed forms are shown in structural formulae herein, open forms are also encompassed by the invention. Similarly, the invention encompasses isomeric forms of the molecules of the invention, including tautomers (e.g. imine/enamine tautomers), conformers, enantiomers, diastereoisomers, etc After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 256].

MODES FOR CARRYING OUT THE INVENTION

Example 1

Modification of Men A Oligosaccharide

Controlled Hydrolysis of MenA Polysaccharide

MenA oligosaccharides were generated by chemical hydrolysis of a MenA polysaccharide solution. Briefly, MenA polysaccharide was solubilised at a final concentration of 10 mg/ml in 50 mM acetate buffer, pH 4.75. The solution was heated at 73° C. until a degree of polymerization (DP) of approximately 10 was reached. The hydrolysis was controlled by monitoring the variation of the optical activity of the solution (α Hg 365 nm) over time in accordance with the following equation: $DP=1/\{0.5817[1-(\alpha_t/\alpha_m)]\}$, where $\alpha_m$ is the average value of the optical rotatory power of 6 samples when the temperature solution is 50° C., and $\alpha_t$ is the optical rotatory power at time t. The hydrolysis was stopped when the α value corresponding to a DP of 10 was reached. At the end of the hydrolysis reaction the solution was cooled at room temperature and the pH corrected to about 6.5.

Size Fractionation of MenA Oligosaccharide

Controlled acidic hydrolysis of MenA polysaccharide generates a polydispersion with the target average DP. For conjugate preparation, the oligosaccharide polydispersion may be further restricted using a two-step size fractionation. These sizing steps typically change the DP of the MenA oligosaccharides from a value of about 10 to a value between 15 and 20, as measured by the molar ratio between total phosphorus (Pt) and terminal monoester phosphate (Pm) values. Pt concentration was determined according to the method described in reference 259 and Pm was determined by measuring the inorganic phosphate released by enzymatic reaction with potato acid phosphatase [260].

Briefly, the MenA hydrolysate was first ultrafiltered through a 30 KDa tangential flow membrane to remove high molecular weight species. During this procedure the product was concentrated about 10-fold and then diafiltered against 13 volumes of 5 mM acetate buffer, pH 6.5. The permeate, containing the desired oligosaccharides, was collected while the retentate was discarded.

In the second step, the permeate was fractionated by anionic exchange column chromatography. This step is designed to remove low Mw species characterized by a DP of less than 6, which may be poorly immunogenic [261]. The oligosaccharide mixture obtained from the 30 KDa ultrafiltration was loaded onto a column packed with Q-Sepharose Fast Flow previously equilibrated with 5 mM sodium acetate, pH 6.5. The ratio oligosaccharide/packed volume was 17 mg/ml packed resin. The column was then washed with 5 column volumes (cv) of the equilibration buffer. A wash of 10 cv of 5 mM sodium acetate buffer/125 mM NaCl, pH 6.5 was then applied to the column to elute oligosaccharides of DP≤6. The desired oligosaccharide fraction was then recovered by elution with 5 mM sodium acetate buffer/ 500 mM NaCl, pH 6.5. Stripping with 5 cv of 2M NaCl and sanitization with 1M NaOH completed the procedure.

Figure 2:
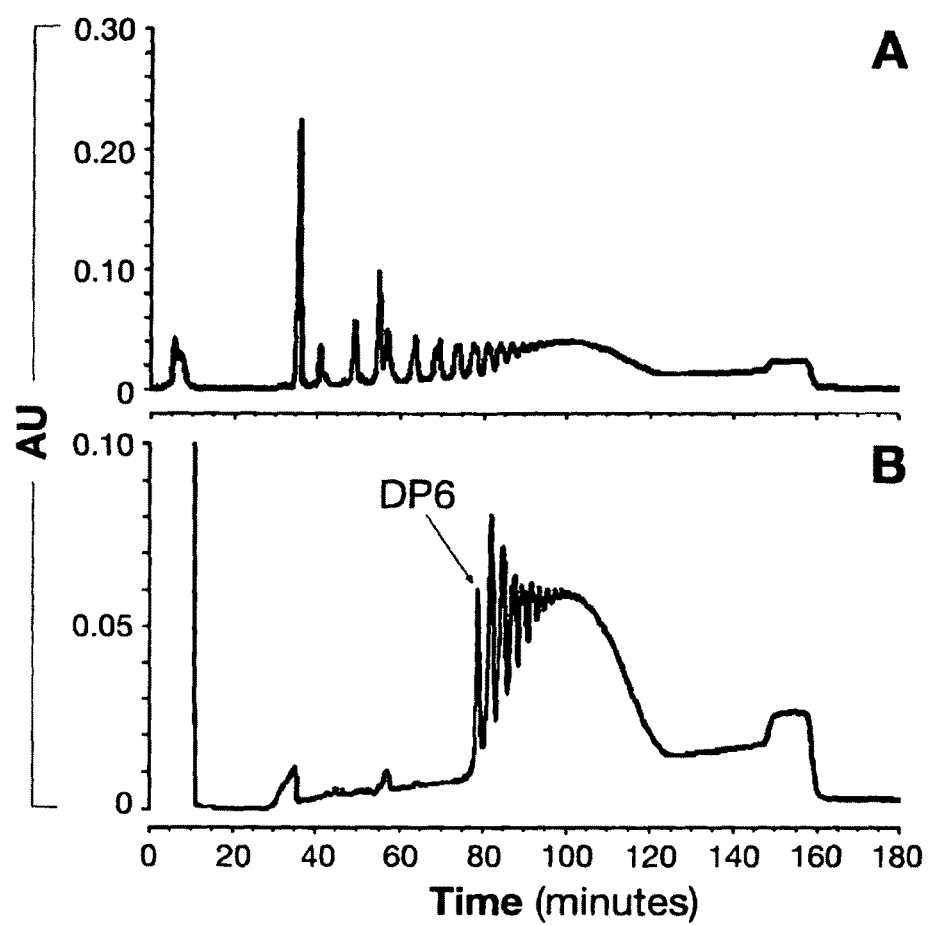
FIG. 2 provides the anion exchange analytical profile at 214 nm of MenA oligosaccharides before (panel A) and after (panel B) sizing.

Analytical anion exchange chromatography was used to measure the oligosaccharide polydispersion before and after the fractionation. Briefly, the polydispersions of MenA oligosaccharide were analyzed by HPLC using a Mono-Q HR 5/5 column. After equilibration with water, 1 ml of sample containing about 1 mg of saccharide was loaded onto the column, which was then developed with a linear gradient form 0 to 60% of NaCl 1 M at the flow rate of 0.5 ml. The chromatogram was monitored at 214 nm. A standard preparation of a monodispersed MenA oligosaccharide having a defined DP of 5 and 6 respectively as evidenced by Mass Spectrometry and $^1$H NMR, was used to identify the presence or removal of oligosaccharides having a DP lower than 6 in the tested polydispersion samples. FIG. 2 shows the analytical profiles of the hydrolysate (panel A) as compared to the sized MenA oligosaccharide (panel B).

Counter Ion Exchange

The Q-Sepharose eluate from the two-step size fractionation procedure was ultrafiltered on a 3 KDa membrane in order to exchange the sodium counter ion with tetrabutylammonium, which confers solubility to the oligosaccharide in non-aqueous solvents. Briefly, the MenA oligosaccharide solution was diafiltered against 4 volumes of 10 mM tetrabutylammoniumbromide followed by 10 volumes of water. The retentate, containing the desired product, was collected and the permeate discarded. Water was removed from the retentate by rotary evaporation.

Chemical Modification of MenA Oligosaccharide

The MenA oligosaccharide was modified using 1,1'-carbonyldiimidazole (CDI) activation followed by reaction with either 1-amino-4,5-pentandiol (APD) alone or APD and 2-aminoethanol (ETA), in order to obtain two different target structures (FIG. 1):
  i) MenA oligosaccharide comprising a 4,5-dihydroxypentylcarbamate blocking group on approximately 10% of the monosaccharide units and a 2-hydroxyethylcarbamate blocking group on approximately 90% of the monosaccharide units (MenA10/90); and
  ii) MenA oligosaccharide comprising a 4,5-dihydroxypentylcarbamate blocking group on approximately 10% of the monosaccharide units (MenA10/0).

Briefly, the MenA oligosaccharide derived from the 3 KDa membrane ultrafiltration described above was solubilised in DMSO to a final concentration of about 10 mg/ml. To this solution a 20-fold molar excess of CDI (relative to the number of moles of MenA monosaccharide units) was added and the solution stirred at room temperature for 2 hrs. The activated oligosaccharide solution was then added to 9 volumes of cold (−20° C.) ethyl acetate followed by a 2 M solution of $CaCl_2$ to a final concentration equimolar with the MenA monosaccharide units. The mixture was stirred for 30 minutes and, after sedimentation of the oligosaccharide, the majority of the supernatant was removed by suction and the pellet recovered by centrifugation, washed 3 times with ethyl acetate and dried under vacuum.

For addition of blocking groups, the activated oligosaccharide was solubilised in DMSO to a final concentrat of 10 mg/ml. To obtain the "MenA10/0" oligosaccharide, a 0.1-fold molar excess (relative to the number of moles of MenA monosaccharide units) of APD was added, and the reaction was stirred for 2 hrs at room temperature. After this time, nineteen volumes of 0.25 M sodium phosphate buffer, pH 6.5 were added under stirring. Any opalescence formed during this operation was removed by filtration through a 0.2 μm membrane. To obtain the "MenA10/90" oligosaccharide, a 0.6-fold molar excess of triethylamine and a 0.1-fold molar excess of APD were added and the reaction was stirred for 2 hrs at room temperature. Subsequently, a 50-fold molar excess (relative to the number of moles of MenA monosaccharide units) of ETA was added and the reaction continued under stirring for a further 2 hrs. Once again, after this time nineteen volumes of 0.25 M sodium phosphate buffer, pH 6.5 were added under stirring and any opalescence removed by filtration through a 0.2 μm membrane.

The crude solutions of derivatised oligosaccharide were purified from the excess of low molecular weight reagents by ultrafiltration on a 3 KDa membrane. The solutions were first concentrated about 20-fold and then diafiltered against 10 volumes of 0.1 M sodium phosphate buffer, pH 7.2, followed by 10 volumes of distilled water. The purified products were recovered from the retentates, with the permeates being discarded.

Confirmation of Chemical Modifications by $^1$H NMR

The chemically-modified MenA oligosaccharides were characterized by NMR to confirm that the desired chemical modifications had taken place.

Figure 3:
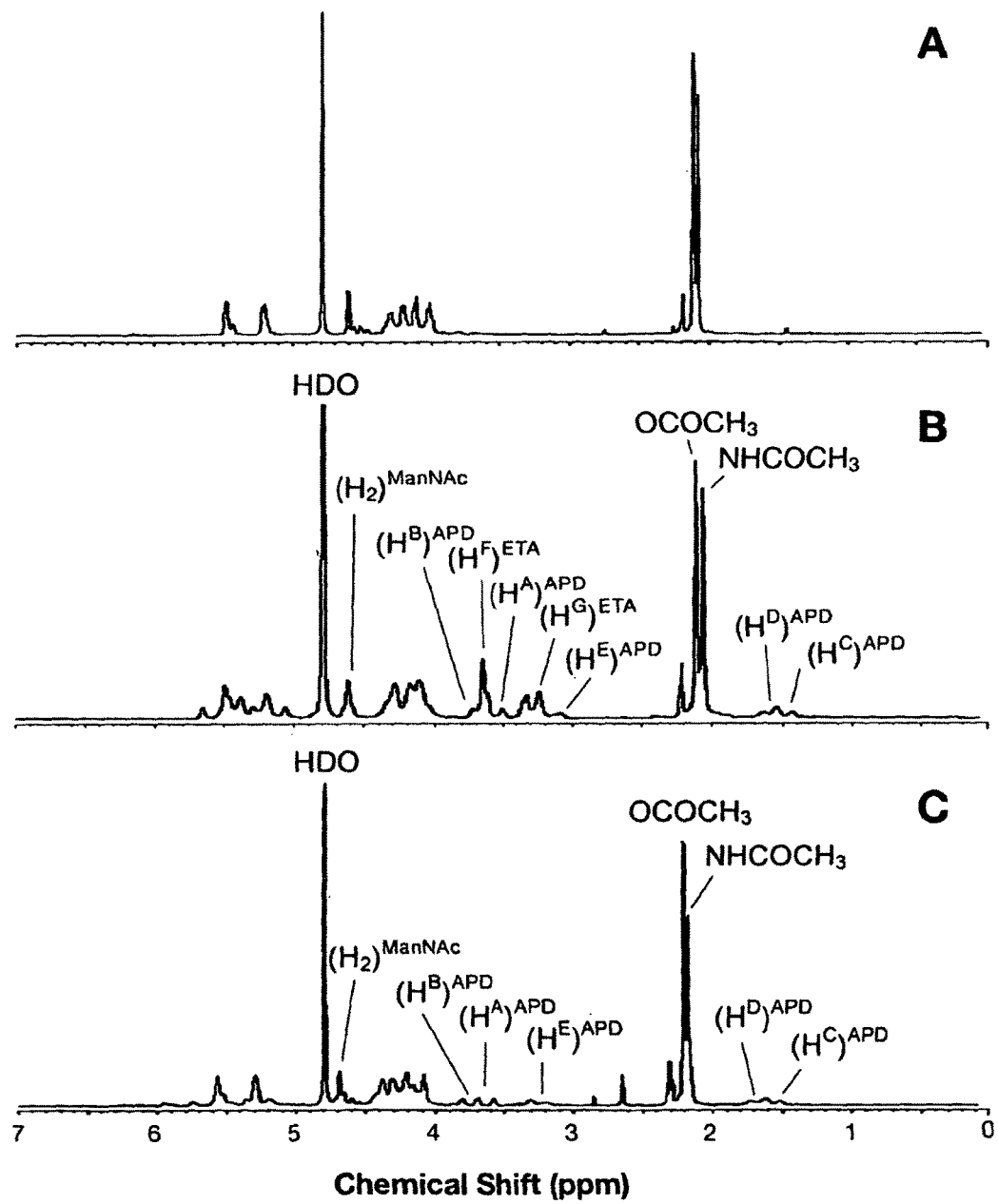
FIG. 3 provides the 600 MHz $^1H$ NMR spectrum at 25° C. of MenA oligosaccharide without chemical modification (panel A), MenA10/90 oligosaccharide (panel B) and MenA10/0 oligosaccharide (panel C).

The $^1$H NMR spectrum of the native MenA oligosaccharide is shown in FIG. 3, panel A. The spectrum is in agreement with the published literature [262, 263]. $^1$H NMR conducted on pure APD and ETA gave the following signals: APD signals: $HOCH_2{}^A CH^B(OH)CH_2{}^C CH_2{}^D CH_2{}^E NH_2$ ($H^A$ at 3.6 ppm, $H^B$ at 3.7 ppm, $H^C$ at 1.5 ppm, $H^D$ at 1.6 ppm, H$^E$ at 2.7 ppm); ETA signals: HOCH$_2$$^F$CH$_2$$^G$NH$_2$ (H$^F$ at 4.4 ppm, H$^G$ at 3.6 ppm). These assignments were used as a guide to identify the APD and ETA signals in the spectra of the derivatised oligosaccharides. The $^1$H NMR spectra of the MenA10/90 oligosaccharide is reported in FIG. 3, panel B. The $^1$H NMR spectrum of the MenA10/0 oligosaccharide is reported in FIG. 3, panel C. The covalent linkage between the ETA or the APD groups and the carbonyl groups introduced in position 4 and/or 3 of N-acetyl-mannosamine was confirmed by the ($^1$H, $^{13}$C) heteronuclear correlation detected in the HSQC spectra. Long-range correlation peaks between the carbonyl groups and the H$^G$ of ETA or H$^E$ of APD were detected. Similarly, the carbonyl groups gave long range correlation with the geminal protons in position 3/4 of N-acetyl-mannosamine. The percentages of APD groups introduced by the chemical treatment were estimated by integration of selected signals coming from APD and MenA. H$^D$+H$^C$ overlapped signals at 1.5 ppm (APD groups) were integrated versus the H$_2$ peak at 4.6 ppm (MenA oligosaccharide). In different experiments from 6% to 14% of MenA monosaccharide units were substituted with APD groups. Following the same approach, ETA groups were estimated by the ratio with H$^F$ overlapped signals at 3.6 ppm (ETA groups) against the H$_2$ peak at 4.6 ppm (MenA oligosaccharide). Due to the partial overlapping with the APD signals (H$^A$ at 3.6 ppm and H$^B$ at 3.7 ppm) the integral of H$^F$ was subtracted by the ¾ of H$^D$+H$^C$ value. In different experiments from 66% to 85% of MenA monosaccharide units were substituted with ETA groups. As expected, in FIG. 3, panel C signals related to ETA groups are not present, which confirms the proposed structure and the suitability of NMR as a tool for structure elucidation and identity assessment. FIG. 3, panel A indicates that O-acetylation is preserved after acidic hydrolysis of serogroup A meningococcal polysaccharide and, although the carbamate groups change the local magnetic field and make the assignment more complicated, the O-acetylation status appears to be maintained after chemical modification (FIG. 3, panels B and C).

Stability of MenA Oligosaccharides

Degradation of MenA oligosaccharide, a consequence of hydrolysis at phosphodiester bonds, results in newly formed phosphomonoester groups. The stability of MenA10/90 and MenA10/0 oligosaccharides was compared with the stability of a native oligosaccharide.

Briefly, solutions of the MenA oligosaccharides, in a concentration range from 1.4 to 3 mg/ml, were incubated at 37° C. in 10 mM histidine buffer, pH 7.2. At different time points over a period of 42 days, the oligosaccharides were analysed for the amount of phosphomonoester generated during storage.

Figure 4:
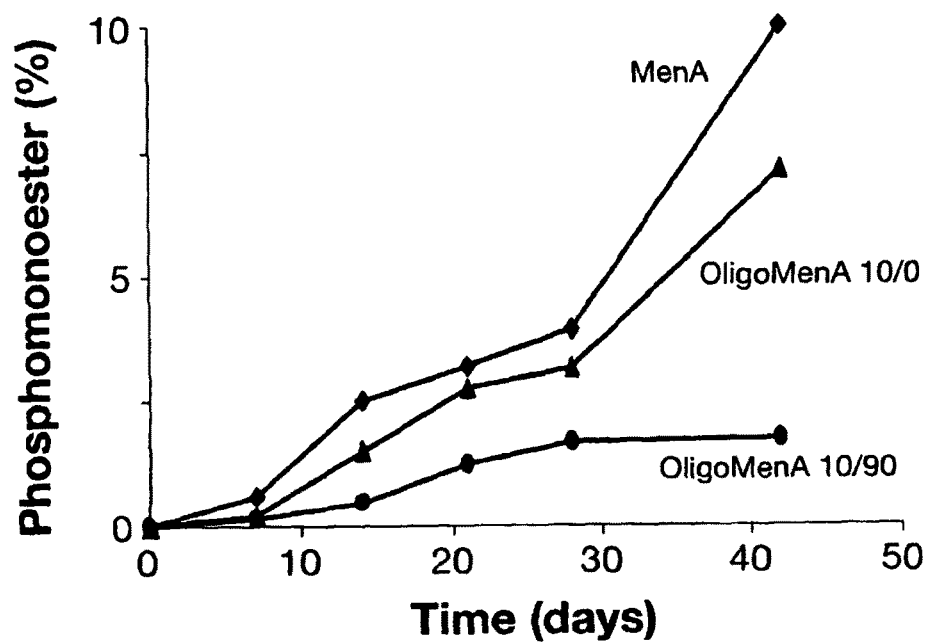
FIG. 4 compares the percentage of phosphomonoester developed during storage at 37° C. by MenA oligosaccharide without chemical modification, MenA10/90 oligosaccharide and MenA10/0 oligosaccharide.

FIG. 4 shows the increment of phosphomonoester groups during storage at 37° C. for the three oligosaccharides mentioned above. The percentage of phosphomonoester was calculated as [Pm(t)−Pm(0)]×100/[(Pt(0)−Pm(0)], where Pm(t) and Pt(t) are the concentrations of phosphomonoester groups and total phosphorus at time t; and Pm(0) and Pt(0) are the concentrations of phosphomonoester groups and total phosphorus at time 0. Total phosphorus (Pt) concentration was determined according to the method described in reference 259 and terminal monoester phosphate (Pm) was determined by measuring the inorganic phosphate released by enzymatic reaction with potato acid phosphatase [260].

The MenA10/90 and MenA10/0 oligosaccharides showed improved stability compared to the native oligosaccharide, as evidenced by the reduced trend to release phosphomonoester groups over the time. These results show that the stability of the MenA oligosaccharide can be enhanced by blocking the hydroxyl groups in position 4 and 3 of N-acetylmannosamine with a blocking group according to the present invention.

Figure 5:
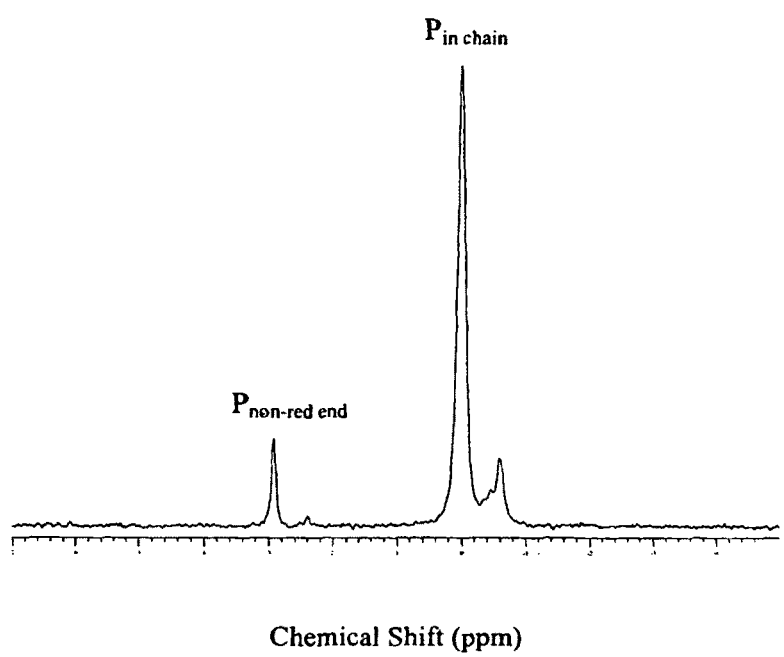
FIG. 5 provides the $^{31}P$ NMR spectrum of MenA oligosaccharide.

Similarly, $^{31}$P NMR analysis [264] was used to evaluate the stability of the modified MenA oligosaccharides in comparison to the native oligosaccharide at 37° C. for 42 days in 10 mM histidine buffer pH 7.2. Briefly, the average degree of depolymerisation (avDP) was determined by the molar ratio between the phosphodiester in chain groups (P$_{in\ chain}$) and the phosphomonoester non-reducing end groups (P$_{non-red\ end}$) (FIG. 5).

avDP=[P$_{in\ chain}$+1]/P$_{non-red\ end}$

Figure 6:
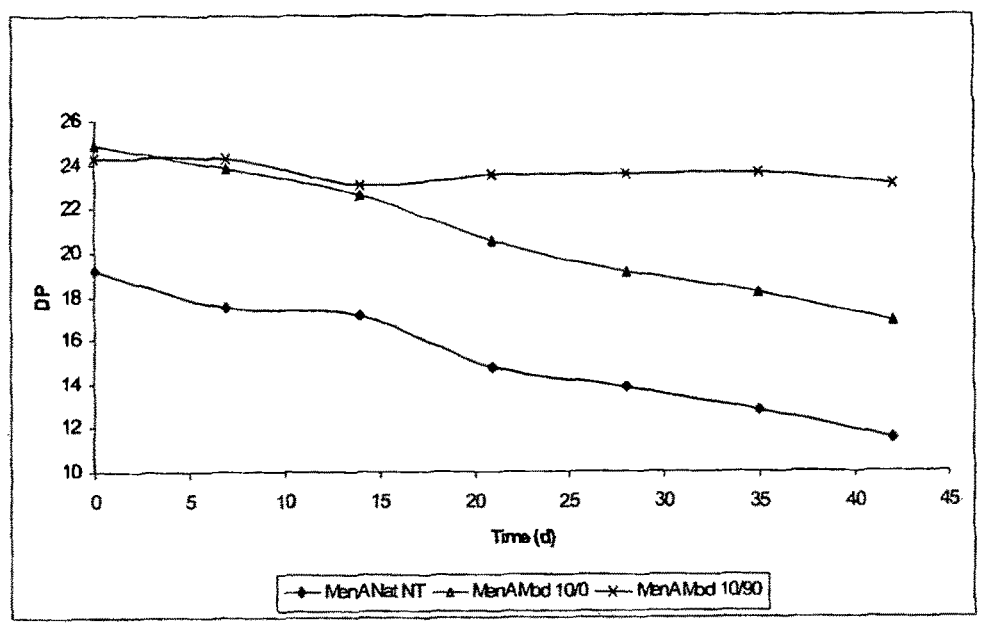
FIG. 6 compares the degree of polymerisation (DP), measured by $^{31}P$ NMR, during storage at 37° C. of MenA oligosaccharide without chemical modification, MenA10/90 oligosaccharide and MenA10/0 oligosaccharide.

Once again, the MenA10/90 and MenA10/0 oligosaccharides showed improved stability compared to the native oligosaccharide, as evidenced by the greater degree of polymerisation at all time points (FIG. 6).

TABLE I

| Sample | avDP | | | | | | |
|---|---|---|---|---|---|---|---|
| | 0 d | 7 d | 14 d | 21 d | 28 d | 35 d | 42 d |
| Oligo MenA Native | 19.2 | 17.5 | 17.1 | 14.7 | 13.8 | 12.8 | 11.5 |
| Oligo MenA10/0 | 24.9 | 23.8 | 22.6 | 20.5 | 19.1 | 18.2 | 16.8 |
| Oligo MenA10/90 | 24.3 | 24.3 | 24.1 | 23.5 | 23.5 | 23.6 | 23.1 |

CRM$_{197}$-MenA Conjugates

Generation of Reactive Aldehydic Groups by Controlled Periodate Oxidation

The vicinal hydroxyl groups of the 4,5-dihydroxypentyl-carbamate blocking groups derived from APD in the MenA10/90 and MenA10/0 oligosaccharides were oxidized by limited sodium periodate treatment to generate reactive aldehydic groups. Briefly, solutions of MenA10/90 and MenA10/0 oligosaccharides in 0.1 M sodium phosphate buffer, pH 7.2, were reacted with 0.1 moles of NaIO$_4$ per mole of MenA monosaccharide units. The reactions was carried out in the dark with stirring, and monitored spectrophotometrically at 225 nm. After about 2 hrs the 225 nm absorbance reached a plateau. The amount of aldehydic groups generated by the reaction was determined by analyzing the equimolar amount of formaldehyde released during oxidation [265]. The reactions were stopped by addition of ethylene glycol to a final concentration equimolar with the NaIO$_4$.

The generation of aldehydic groups was almost quantitative as compared to the initial number of 4,5-dihydroxypentylcarbamate blocking groups.

Purification of Oxidized Oligosaccharides

The oxidized oligosaccharides were purified by ultrafiltration on a 3 KDa membrane. The solutions were concentrated 2-fold and then diafiltered against 10 volumes of 0.5 M NaCl followed by 10 volumes of distilled water. The retentate, containing the desired product, was collected and the permeate discarded. Water was removed from the retentate by rotary evaporation.

Conjugation to CRM$_{197}$

Figure 1:
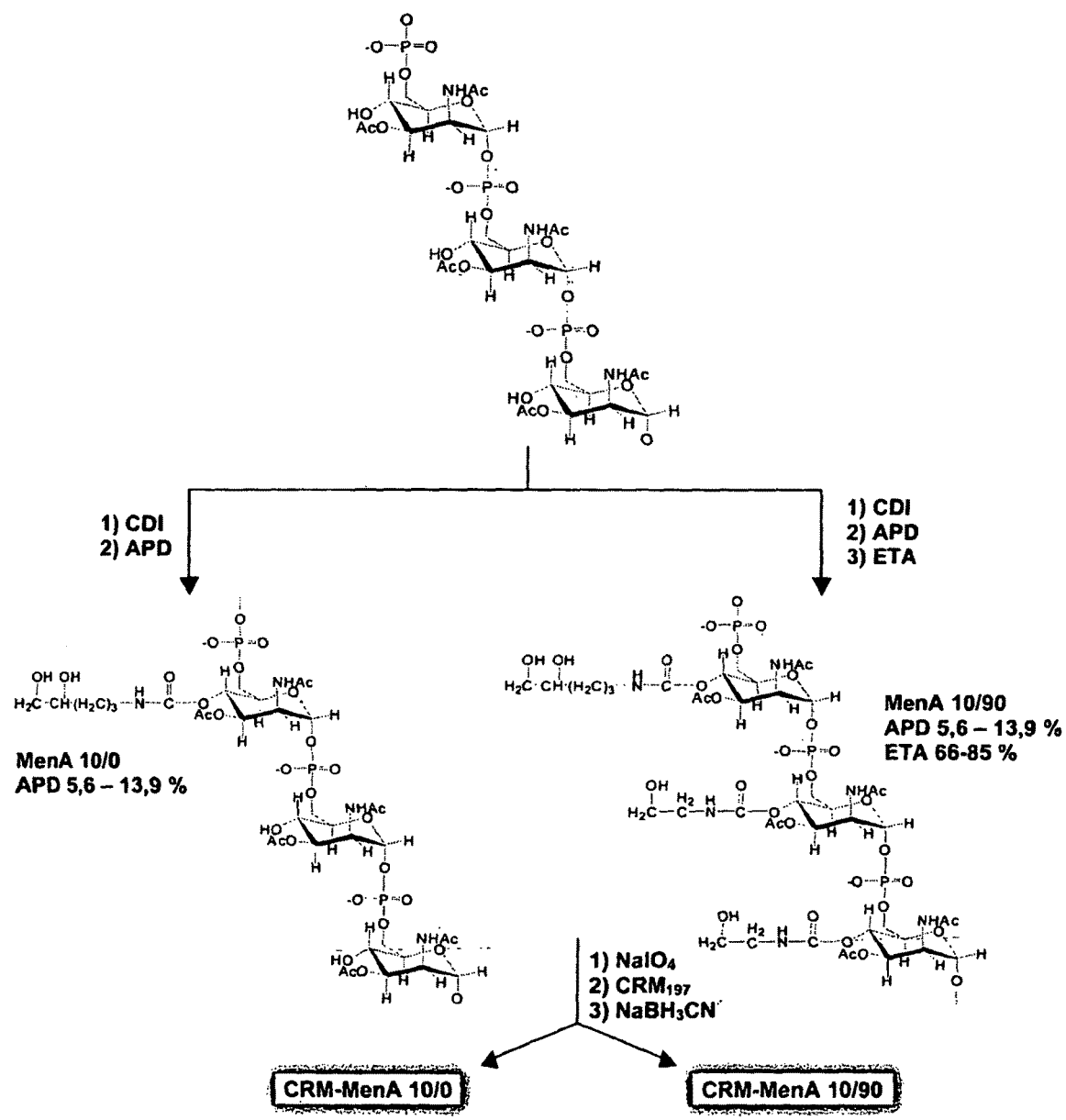
FIG. 1 provides a scheme for the chemical synthesis of $CRM_{197}$-MenA conjugates. The prevalent structures of "MenA10/90" (MenA oligosaccharide comprising a 4,5-dihydroxypentylcarbamate blocking group on approximately 10% of the monosaccharide units and a 2-hydroxyethylcarbamate blocking group on approximately 90% of the monosaccharide units) and "MenA10/0" (MenA oligosaccharide comprising a 4,5-dihydroxypentylcarbamate blocking group on approximately 10% of the monosaccharide units) are represented.

The oxidized MenA oligosaccharides were conjugated to CRM$_{197}$, a non-toxic mutant of the diphtheria toxin [266], via reductive amination to obtain CRM-MenA10/90 and CRM-MenA10/0 respectively (FIG. 1).

Briefly, the oxidized MenA oligosaccharides were solubilised in a 50 mg/ml solution of CRM$_{197}$ at a ratio of 13 moles of aldehydic groups per mole of protein. 100 mM sodium phosphate buffer, pH 7.2, was added to obtain a final protein concentration of 30 mg/ml. A 2M solution of NaBH$_3$CN in 10 mM sodium phosphate buffer, pH 7.2, was then added to obtain a 70-fold molar excess of NaBH$_3$CN with respect to the aldehydic groups. The reactions were carried out for 3 days at 37° C. Fourteen volumes of 10 mM sodium phosphate buffer, pH 7.2, were then added, followed by a 25-fold molar excess of NaBH$_4$ (relative to the relative to the number of moles of aldehydic groups). The pH was controlled at 8.5 and the mixtures were stirred for 2 hrs at room temperature in order to quench any residual aldehydic groups. At the end of the quenching step, the pH was corrected again to 7.2, and the solutions filtered through a 0.2 μm-pore membrane.

Purification of Conjugates

The conjugates were purified from the excess of reagents and residual, unreacted oligosaccharides by ultrafiltration on a 30 KDa membrane. The reaction mixtures were diafiltered against 100 volumes of 0.01 M sodium phosphate buffer, pH 7.2, followed by 50 volumes of 10 mM histidine, pH 7.2. The solutions containing the purified conjugates were then filtered through a 0.2 μm-pore membrane and stored at 2-8° C.

Confirmation of Conjugation to CRM$_{197}$

Figure 7:
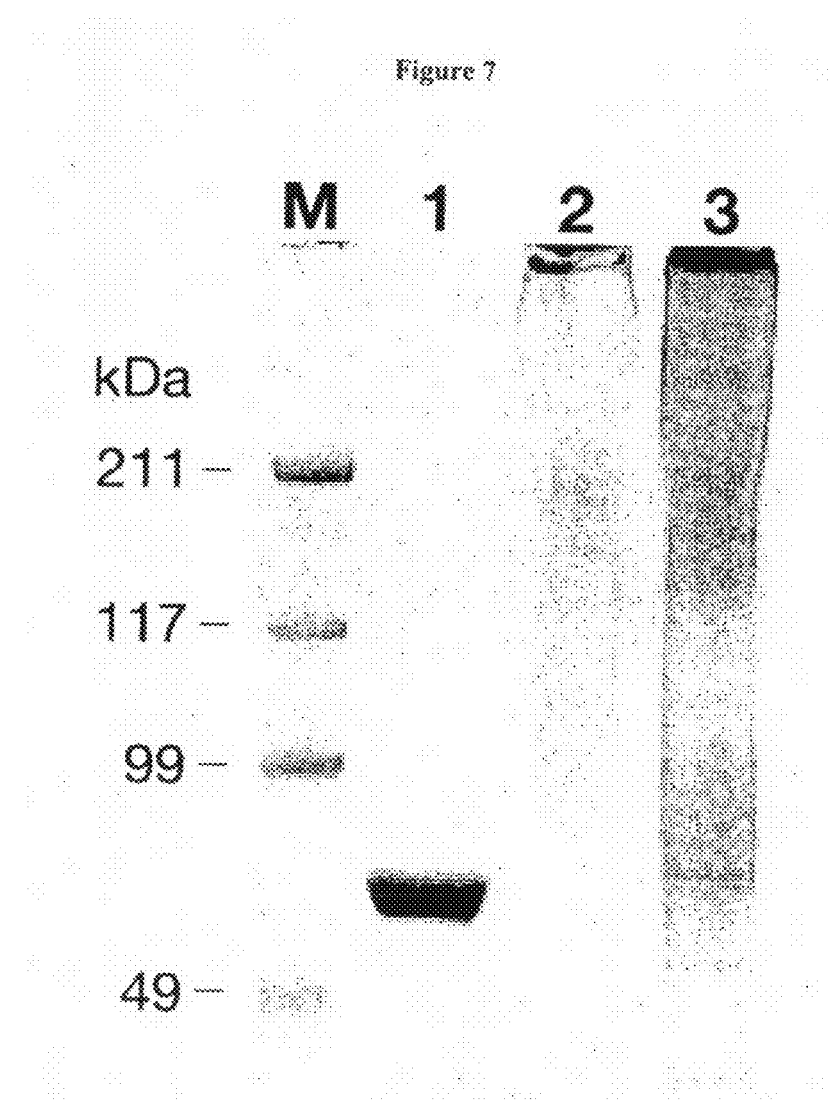
FIG. 7 provides the SDS-Page profile of CRM-MenA oligosaccharide conjugates: Lane M—Mw Markers; Lane 1—CRM; Lane 2—CRM-MenA10/90; and Lane 3—CRM-MenA10/0.

Conjugation of the MenA oligosaccharides to CRM$_{197}$ was demonstrated by SDS-Page (FIG. 7). SDS-Page was carried out according to reference 267 using 7.5% acrylamide for stacking and 7.5% acrylamide for the separating gel. Before electrophoresis, samples were treated 1:4 with sample buffer and boiled for 10 min. Electrophoresis was carried out at 200 V constant voltage for about 40 min. Gels were developed with a Coomassie stain solution for approximately 20 min and destained in acetic acid/EtOH solution (7/40%) for approximately 4 hrs.

The profile of the conjugates in FIG. 7 is shifted towards higher molecular weights compared to CRM$_{197}$, and is markedly different from CRM$_{197}$. The SDS-Page analysis also demonstrates the presence of high molecular weight material. This material may be formed during the conjugation reaction, which allows multiple attachment points of the CRM$_{197}$ per oligosaccharide molecule.

The conjugates were also analyzed for saccharide and protein content. Saccharide/protein ratios ranging from 0.20 to 0.32 (wt/wt) were observed.

Stability of CRM$_{197}$-MenA Conjugates

The stability of the CRM$_{197}$-MenA conjugates was determined by measuring the release of unconjugated saccharide over the time, which results from hydrolysis of the phosphodiester bonds.

Centricon 30 devices (2 ml capacity) were conditioned by rinsing with 1 ml distilled water and spinning twice. 60 μl saline was added to 940 μl sample (CRM-MenA10/90 or CRM-MenA10/0) containing about 0.3 mg/ml of saccharide. Total phosphorus content was measured as described above before adding the mixtures to the devices. The devices were spun at 1942 g until 100-200 μl of solution was left in the retentate chamber, and then washed with 2×1 ml of saline and spun again. The solution in the permeate chamber was recovered and the sample volume adjusted with saline to 3 ml. The permeate derived from each sample was analyzed for total phosphorus content as described above.

The value (P2/P1)×100, where P1 is the total phosphorus before centricon treatment and P2 is the total phosphorus after centricon treatment, represents the percentage of free saccharide. Spiking experiments to demonstrate the recovery of the free oligosaccharide through the membrane were conducted by adding 60 μl of about 2 mg/ml oligosaccharide to 940 μl of sample or saline and then applying the separation procedure described above. Recovery was consistently above 80%.

Figure 8:
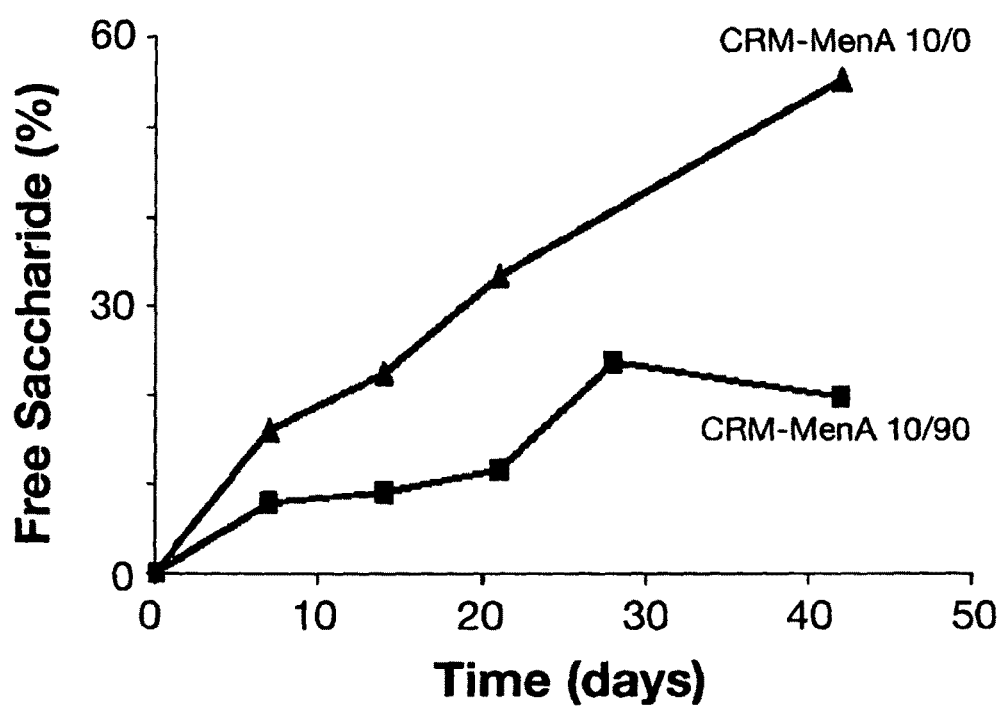
FIG. 8 compares the free saccharide (FS) released during storage at 37° C. from CRM-MenA10/90 oligosaccharide conjugates and CRM-MenA10/0 oligosaccharide conjugates.

FIG. 8 shows that the conjugate CRM-MenA10/90 showed a reduced tendency to release free saccharide compared to CRM-MenA10/0. FS (Free saccharide) is calculated as FS % (t)–FS % (0) where FS % (t) and FS % (0) are the free saccharide percentages at time t and 0 respectively.

The stability of the CRM$_{197}$-MenA conjugates was also determined by measuring phosphomonoester generation during storage. Briefly, solutions of the conjugates, in a concentration range from 157 to 253 μg/ml, were incubated at 37° C. in 10 mM histidine buffer, pH 7.2. At different time points over a period of 42 days, the conjugates were analysed for the amount of phosphomonoester generated during storage.

Figure 9:
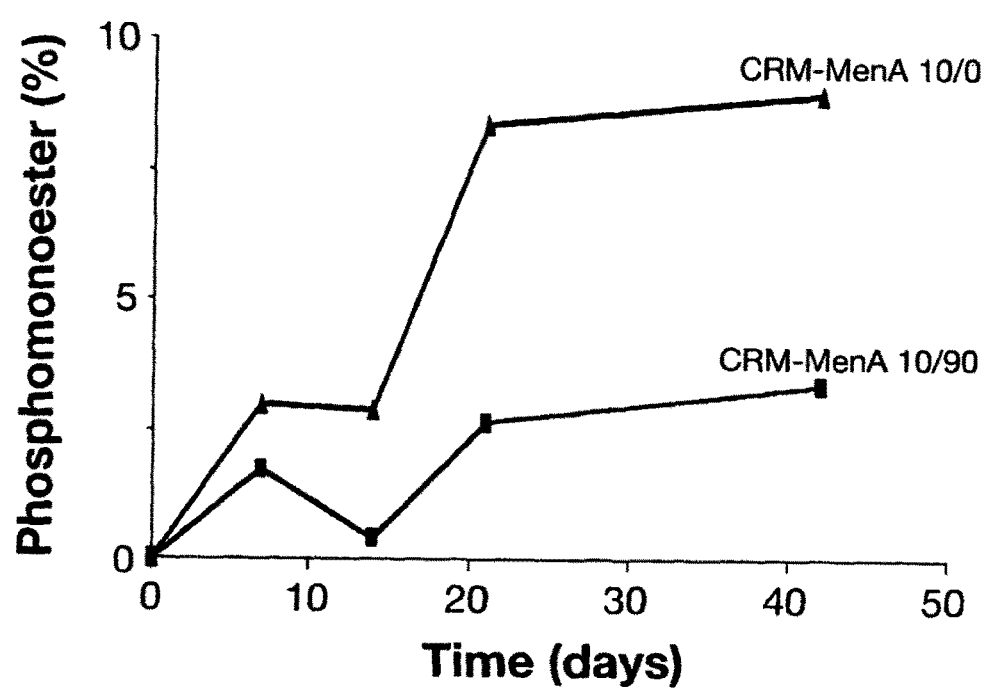
FIG. 9 compares the percentage of phosphomonoester developed during storage at 37° C. by CRM-MenA10/90 oligosaccharide conjugates and CRM-MenA10/0 oligosaccharide conjugates.

FIG. 9 shows the increment of phosphomonoester groups during storage at 37° C. for the two conjugates mentioned above. The percentage of phosphomonoester was calculated as described above. The conjugate CRM-MenA10/90 showed a reduced tendency to generate phosphomonoester compared to CRM-MenA10/0.

Immunogenicity of CRM-MenA Conjugates

In order to assess the ability of the MenA conjugates to elicit antibodies recognizing the native MenA capsular polysaccharide, immunogenicity experiments were conducted in mice.

Vaccine Formulation

CRM-MenA10/90 and CRM MenA10/0 conjugates were mixed with sodium phosphate buffer and a AlPO$_4$ suspension to obtain final concentrations of 20 μg/ml saccharide and 0.6 mg/ml Al$^{3+}$ in 10 mM sodium phosphate buffer, pH 7.2. For non-adjuvanted formulations, the AlPO$_4$ suspension was replaced with sodium phosphate buffer. Before immunization, the resultant vaccines were diluted 1:5 with saline.

Immunization of Mice

Groups of 8 Balb/c mice, females of 6-8 weeks, were immunized two or three times s.c. with 0.5 ml of conjugate vaccines containing 2 μg of saccharide. In the case of the two-injection schedule, the interval between the first and the second dose was four weeks. Bleedings were performed before the immunization and two weeks after the second dose. In the case of the three doses schedule, vaccines were given at 0, 14 and 28 days and bleedings were performed at time zero, one day before (post 2 doses sera) and 14 days after (post 3 doses sera) the third immunization.

Immunogenicity

The sera from the immunized mice were analyzed for specific anti-MenA capsular polysaccharide total IgG antibodies and for complement mediated serum bactericidal activity (SBA) against *Neisseria meningitidis* serogroup A.

Specific anti-MenA capsular polysaccharide total IgG antibodies were determined essentially according the method of reference 268, adapted for animal sera analysis. Each individual mouse serum was analyzed in duplicate by a titration curve. Anti-MenA polysaccharide titers were calculated as Mouse Elisa Unit (MEU)/ml using software based on the Reference Line Assay Method. Geometric mean titers (GMT) were calculated for each immunization groups.

SBA was measured on post II and post III (where appropriate) sera pools for each immunization group. The standard SBA protocol was based on the inoculum of the test bacterial strain (MenA F8238) in Mueller Hinton Broth with the addition of 0.25% glucose. The bacterial culture was incubated at 37° C. in the presence of 5% CO$_2$ and growth stopped when the bacteria reached the early exponential phase of growth, around 0.220-0.240 $OD_{600}$. The bacteria were then diluted to $10^{-4}$ with 1% BSA in GBBS buffer and incubated for 1 hour at 37° C. with 5% $CO_2$ in the presence of heat inactivated sera pools (30 minutes at 56° C.) and 25% baby rabbit serum as a source of complement. The reaction mixtures were then plated on Mueller Hinton agar and incubated overnight at 37° C. Bactericidal titres were expressed as the reciprocal serum dilution yielding 50% killing of the bacteria.

Table II shows the anti-MenA capsular polysaccharide total IgG titers expressed as GMT (+/−95 confidence limits) as measured by ELISA and the SBA titers induced by CRM-MenA10/90, and CRM-MenA10/0. Both conjugates were capable of inducing in mice specific anti-MenA polysaccharide antibodies with bactericidal functional activity.

TABLE II

| Vaccine | Post 2 ELISA Titre GMT (+/−95% CI) | Post 2 SBA Titre |
|---|---|---|
| CRM-MenA 10/0 lot 5/AlPO4 | 346 (230; 520) | >4096 < 8192 |
| CRM-MenA 10/90 lot 5/AlPO4 | 270 (217; 336) | 4096 |

In a second experiment, the immunogenicity in mice of CRM-MenA10/90 was tested with and without $AlPO_4$. The immunogenicity of the CRM-MenA10/90 is confirmed in Table III, which shows the specific anti-MenA IgG antibody titers induced after two and three immunizations and the complement mediated bactericidal activity of these antibodies. Pre-immunization titres were found to be negative (SBA<4). These data suggest that the presence of the adjuvant enhances the antibody response. The immunogenicity observed in the conjugate is clearly a consequence of the chemical conjugation of the oligosaccharide to the protein carrier, as a physical mixture of MenA oligosaccharide, $CRM_{197}$ and $AlPO_4$ was not immunogenic.

TABLE III

| Vaccine | Post 2 ELISA Titre GMT (+/−95% CI) | Post 3 ELISA Titre GMT (+/−95% CI) | Post 2 SBA Titre | Post3 SBA Titre |
|---|---|---|---|---|
| CRM-MenA10/90 lot11 AlPO4 | 867 (585; 1285) | 1299 (1008; 1675) | 2048 | 4096 |
| CRM-MenA 10/90 lot 11 | 388 (249; 604) | 426 (241; 751) | 1024 | 2048 |
| OligoMenA10/90 lot 11 + $CRM_{197}$ + $AlPO_4$ (physical mix of unconjugated antigens) | 2 | 2 | <4 | <4 |

Example 2

Modification of Men A Polysaccharide

Chemical Modification of MenA Polysaccharide 20 mg of native MenA capsular polysaccharide (0.072 mmol) was added to 170 mg (2.5 mmol) of imidazole and 1 mL of $CH_3CN$. Stirring with a magnetic bar, 163 µL (1.59 mmol) of acetic anhydride was added and the reaction was incubated at 55° C. for 21 h. The imidazole:acetic anhydride molar ratio was 2:4. A diafiltration step using a Centricon cellulose membrane (1 kDa molecular weight cut-off) against Milli-Q water (1:7 vol/vol) was used to purify the reaction product. The material was finally dried under vacuum (SpeedVac).

Confirmation of Chemical Modifications by $^1H$ and $^{13}C$ NMR

To establish the degree of acetylation, a complete structural characterisation of the modified MenA capsular polysaccharide was carried out by $^1H$ and $^{13}C$ NMR spectroscopy.

Quantitative NMR analysis was used to quantify the level of O-acetylation of the saccharide chains. The O-acetylation percentage was estimated by integration of $H_2^{3OAc}$ peak (proton at position C-2 of the N-acetyl-mannosamine residues O-acetylated at C-3), $H_2^{4OAc}$ peak (proton at position C-2 of the N-acetyl-mannosamine residues O-acetylated at C-4) and $H_2^{deOAc}$ peak (proton at position C-2 of the N-acetyl-mannosamine residues without O-acetylation), in comparison to $H_1$ (proton at position C-1 of the N-acetyl-mannosamine residues). The total O-acetylation level was obtained by the sum of $H_2^{3OAc}$ and $H_2^{4OAc}$ peak integrations.

% O-Acetylation=$[H_2^{3OAc}+H_2^{4OAc}]/[H_1^{deOAc}]$

Moreover, the O-acetylation percentage was estimated by integration of $H_2^{3OAc}/H_2^{4OAc}$ peak (proton at position C-3 of the N-acetyl-mannosamine residues O-acetylated at C-3 and proton at position C-4 of the N-acetyl-mannosamine residues O-acetylated at C-4), in comparison to $H_1$ (proton at position C-1 of the N-acetyl-mannosamine residues).

% O-Acetylation=$[H_2^{3OAc}/H_2^{4OAc}]/[H_1^{OAc}+H_1^{deOAc}]$

Stability of MenA Polysaccharides $^{31}P$ NMR analysis was used to evaluate the stability of the fully acetylated modified MenA capsular polysaccharide in comparison to the native polysaccharide and corresponding oligosaccharide at 37° C. for 42 days in 10 mM histidine buffer pH 7.2, as described above.

The fully O-acetylated modified MenA polysaccharide was much more stable than the native capsular polysaccharide and corresponding oligosaccharide.

TABLE IV

| Sample | avDP | | | | | | |
|---|---|---|---|---|---|---|---|
| | 0 d | 7 d | 14 d | 21 d | 28 d | 35 d | 42 d |
| Poly MenA Native | >50 | >50 | 44.6 | 29.6 | 26.9 | 20.8 | 18.3 |
| Oligo MenA Native | 17.3 | 15.5 | 13.0 | 12.0 | 11.0 | 10.4 | 9.6 |
| Poly MenA Fully Ac | >50 | >50 | >50 | >50 | >50 | >50 | >50 |

These results confirm that the stability of the MenA oligosaccharide can be enhanced by blocking the hydroxyl groups in position 4 and 3 of N-acetylmannosamine with a blocking group according to the present invention.

It will be understood that the invention has been described by way of example only and modifications may be made whilst remaining within the scope and spirit of the invention.

REFERENCES

The Contents of which are Hereby Incorporated by Reference

[1] U.S. Pat. No. 4,711,779
[2] U.S. Pat. No. 4,761,283
[3] U.S. Pat. No. 4,882,317
[4] WO 03/080678
[5] Berkin et al. (2002) Chemistry 8:4424-33
[6] Ramsay et al. (2001) Lancet 357(9251):195-6
[7] Lindberg (1999) Vaccine 17 Suppl 2:S28-36
[8] Buttery & Moxon (2000) J R Coll Physicians Lond 34:163-8
[9] Ahmad & Chapnick (1999) Infect Dis Clin North Am 13:113-33, vii
[10] Goldblatt (1998) J. Med. Microbiol. 47:563-567
[11] EP-B-0 477 508
[12] U.S. Pat. No. 5,306,492
[13] WO98/42721
[14] Dick et al. in Conjugate Vaccines (eds. Cruse et al.) Karger, Basel, 1989, Vol. 10, 48-114
[15] Hermanson Bioconjugate Techniques, Academic Press, San Diego Calif. (1996)
[16] U.S. Pat. No. 4,356,170
[17] U.S. Pat. No. 4,695,624
[18] Bethell G. S. et al., J. Biol. Chem., 1979, 254, 2572-4
[19] Hearn M. T. W., J. Chromatogr., 1981, 218, 509-18
[20] Mol. Immunol., 1985, 22, 907-919
[21] EP-A-0208375
[22] WO00/10599
[23] Gever et al., Med. Microbiol. Immunol, 165: 171-288 (1979).
[24] U.S. Pat. No. 4,057,685.
[25] U.S. Pat. Nos. 4,673,574; 4,761,283; 4,808,700.
[26] U.S. Pat. No. 4,459,286.
[27] U.S. Pat. No. 4,965,338
[28] U.S. Pat. No. 4,663,160.
[29] Research Disclosure, 453077 (January 2002)
[30] EP-A-0372501
[31] EP-A-0378881
[32] EP-A-0427347
[33] WO93/17712
[34] WO94/03208
[35] WO98/58668
[36] EP-A-0471177
[37] WO00/56360
[38] WO91/01146
[39] WO00/61761
[40] WO01/72337
[41] Lei et al. (2000) Dev Biol (Basel) 103:259-264
[42] WO00/38711
[43] WO99/42130
[44] Gennaro (2000) Remington: The Science and Practice of Pharmacy. 20th edition, ISBN: 0683306472.
[45] Nony et al. (2001) Vaccine 27:3645-51.
[46] Greenbaum et al. (2004) Vaccine 22:2566-77.
[47] Zurbriggen et al. (2003) Expert Rev Vaccines 2:295-304.
[48] Piascik (2003) J Am Pharm Assoc (Wash D.C.). 43:728-30.
[49] Mann et al. (2004) Vaccine 22:2425-9.
[50] Halperin et al. (1979) Am J Public Health 69:1247-50.
[51] Herbert et al. (1979) J Infect Dis 140:234-8.
[52] Chen et al. (2003) Vaccine 21:2830-6.
[53] U.S. Pat. No. 6,355,271.
[54] WO00/23105.
[55] WO01/22972.
[56] Kandimalla et al. (2003) Nucleic Acids Research 31:2393-2400.
[57] WO02/26757.
[58] WO99/62923.
[59] Krieg (2003) Nature Medicine 9:831-835.
[60] McCluskie et al. (2002) FEMS Immunology and Medical Microbiology 32:179-185.
[61] WO98/40100.
[62] U.S. Pat. No. 6,207,646.
[63] U.S. Pat. No. 6,239,116.
[64] U.S. Pat. No. 6,429,199.
[65] Kandimalla et al. (2003) Biochemical Society Transactions 31 (part 3):654-658.
[66] Blackwell et al. (2003) J Immunol 170:4061-4068.
[67] Krieg (2002) Trends Immunol 23:64-65.
[68] WO01/95935.
[69] Kandimalla et al. (2003) BBRC 306:948-953.
[70] Bhagat et al. (2003) BBRC 300:853-861.
[71] WO03/035836.
[72] Myers et al. (1990) pages 145-156 of Cellular and molecular aspects of endotoxin reactions.
[73] Ulrich (2000) Chapter 16 (pages 273-282) of reference 132.
[74] Johnson et al. (1999) J Med Chem 42:4640-9.
[75] Baldrick et al. (2002) Regulatory Toxicol Pharmacol 35:398-413.
[76] UK patent application GB-A-2220211.
[77] U.S. Pat. No. 4,680,338.
[78] U.S. Pat. No. 4,988,815.
[79] WO92/15582.
[80] Stanley (2002) Clin Exp Dermatol 27:571-577.
[81] Wu et al. (2004) Antiviral Res. 64(2):79-83.
[82] Vasilakos et al. (2000) Cell Immunol. 204(1):64-74.
[83] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[84] Jones (2003) Curr Opin Investig Drugs 4:214-218.
[85] WO2004/060308.
[86] WO2004/064759.
[87] U.S. Pat. No. 6,924,271.
[88] US2005/0070556.
[89] U.S. Pat. No. 5,658,731.
[90] U.S. Pat. No. 5,011,828.
[91] WO2004/87153.
[92] U.S. Pat. No. 6,605,617.
[93] WO02/18383.
[94] WO2004/018455.
[95] WO03/082272.
[96] WO2006/002422.
[97] Johnson et al. (1999) Bioorg Med Chem Lett 9:2273-2278.
[98] Evans et al. (2003) Expert Rev Vaccines 2:219-229.
[99] Andrianov et al. (1998) Biomaterials 19:109-115.
[100] Payne et al. (1998) Adv Drug Delivery Review 31:185-196.
[101] U.S. Pat. No. 5,057,540.
[102] WO96/33739.
[103] EP-A-0109942.
[104] WO96/11711.
[105] WO00/07621.
[106] Barr et al. (1998) Advanced Drug Delivery Reviews 32:247-271.

[107] Sjolanderet et al. (1998) *Advanced Drug Delivery Reviews* 32:321-338.
[108] Pizza et al. (2000) *Int J Med Microbiol* 290:455-461.
[109] WO95/17211.
[110] WO98/42375.
[111] Singh et al] (2001) *J Cont Release* 70:267-276.
[112] WO99/27960.
[113] U.S. Pat. No. 6,090,406
[114] U.S. Pat. No. 5,916,588
[115] EP-A-0626169.
[116] WO99/52549.
[117] WO01/21207.
[118] WO01/21152.
[119] Signorelli & Hadden (2003) *Int Immunopharmacol* 3(8):1177-86.
[120] WO2004/064715.
[121] Cooper (1995) *Pharm Biotechnol* 6:559-80.
[122] WO03/011223.
[123] Meraldi et al. (2003) *Vaccine* 21:2485-2491.
[124] Pajak et al. (2003) *Vaccine* 21:836-842.
[125] U.S. Pat. No. 6,586,409.
[126] Wong et al. (2003) *J Clin Pharmacol* 43(7):735-42.
[127] US2005/0215517.
[128] WO90/14837.
[129] Podda & Del Giudice (2003) *Expert Rev Vaccines* 2:197-203.
[130] Podda (2001) *Vaccine* 19: 2673-2680.
[131] *Vaccine Design: The Subunit and Adjuvant Approach* (eds. Powell & Newman) Plenum Press 1995 (ISBN 0-306-44867-X).
[132] *Vaccine Adjuvants: Preparation Methods and Research Protocols* (Volume 42 of *Methods in Molecular Medicine* series). ISBN: 1-59259-083-7. Ed. O'Hagan.
[133] Allison & Byars (1992) *Res Immunol* 143:519-25.
[134] Hariharan et al. (1995) *Cancer Res* 55:3486-9.
[135] WO95/11700.
[136] U.S. Pat. No. 6,080,725.
[137] WO2005/097181.
[138] International patent application WO 03/007985.
[139] WO01/52885.
[140] Bjune et al. (1991) *Lancet* 338(8775):1093-1096.
[141] Fukasawa et al. (1999) *Vaccine* 17:2951-2958.
[142] Rosenqvist et al. (1998) *Dev. Biol. Stand.* 92:323-333.
[143] Covacci & Rappuoli (2000) *J. Exp. Med.* 19:587-592.
[144] WO93/18150.
[145] Covacci et al. (1993) *Proc. Natl. Acad. Sci. USA* 90: 5791-5795.
[146] Tummuru et al. (1994) *Infect. Immun.* 61:1799-1809.
[147] Marchetti et al. (1998) *Vaccine* 16:33-37.
[148] Telford et al. (1994) *J. Exp. Med.* 179:1653-1658.
[149] Evans et al. (1995) *Gene* 153:123-127.
[150] WO96/01272 & WO96/01273, especially SEQ ID NO:6.
[151] WO97/25429.
[152] WO98/04702.
[153] Watson (2000) *Pediatr Infect Dis J* 19:331-332.
[154] Rubin (2000) *Pediatr Clin North Am* 47:269-285, v.
[155] Jedrzejas (2001) *Microbiol Mol Biol Rev* 65:187-207.
[156] Bell (2000) *Pediatr Infect Dis J* 19:1187-1188.
[157] Iwarson (1995) *APMIS* 103:321-326.
[158] Gerlich et al. (1990) *Vaccine* 8 Suppl:S63-68 & 79-80.
[159] Hsu et al. (1999) *Clin Liver Dis* 3:901-915.
[160] Gustafsson et al. (1996) *N. Engl. J. Med.* 334:349-355.
[161] Rappuoli et al. (1991) *TIBTECH* 9:232-238.
[162] *Vaccines* (1988) eds. Plotkin & Mortimer. ISBN 0-7216-1946-0.
[163] Del Guidice et al. (1998) *Molecular Aspects of Medicine* 19:1-70.
[164] Sutter et al. (2000) *Pediatr Clin North Am* 47:287-308.
[165] Zimmerman & Spann (1999) *Am Fam Physician* 59:113-118, 125-126.
[166] Lindberg (1999) *Vaccine* 17 Suppl 2:S28-36.
[167] Buttery & Moxon (2000) *J R Coll Physicians Lond* 34:163-168.
[168] Ahmad & Chapnick (1999) *Infect Dis Clin North Am* 13:113-133, vii.
[169] Goldblatt (1998) *J. Med. Microbiol.* 47:563-567.
[170] European patent 0477508.
[171] U.S. Pat. No. 5,306,492.
[172] WO98/42721.
[173] *Conjugate Vaccines* (eds. Cruse et al.) ISBN 3805549326, particularly vol. 10:48-114.
[174] Hermanson (1996) *Bioconjugate Techniques ISBN:* 0123423368 or 012342335X.
[175] WO02/02606.
[176] Kalman et al. (1999) *Nature Genetics* 21:385-389.
[177] Read et al. (2000) *Nucleic Acids Res* 28:1397-406.
[178] Shirai et al. (2000) *J. Infect. Dis.* 181(Suppl 3):S524-S527.
[179] WO99/27105.
[180] WO00/27994.
[181] WO00/37494.
[182] WO99/28475.
[183] Ross et al. (2001) *Vaccine* 19:4135-4142.
[184] Dreesen (1997) *Vaccine* 15 Suppl:S2-6.
[185] *MMWR Morb Mortal Wkly Rep* 1998 Jan. 16; 47(1): 12, 19.
[186] McMichael (2000) *Vaccine* 19 Suppl 1:S101-107.
[187] Schuchat (1999) *Lancet* 353(9146):51-6.
[188] WO02/34771.
[189] Dale (1999) *Infect Dis Clin North Am* 13:227-43, viii.
[190] Ferretti et al. (2001) *PNAS USA* 98: 4658-4663.
[191] Kuroda et al. (2001) *Lancet* 357(9264):1225-1240; see also pages 1218-1219.
[192] *J Toxicol Clin Toxicol* (2001) 39:85-100.
[193] Demicheli et al. (1998) *Vaccine* 16:880-884.
[194] Stepanov et al. (1996) *J Biotechnol* 44:155-160.
[195] EP-A-0139417.
[196] Harper et al. (2004) *Lancet* 364(9447):1757-65.
[197] Ingram (2001) *Trends Neurosci* 24:305-307.
[198] Rosenberg (2001) *Nature* 411:380-384.
[199] Moingeon (2001) *Vaccine* 19:1305-1326.
[200] Robinson & Torres (1997) *Seminars in Immunology* 9:271-283.
[201] Donnelly et al. (1997) *Annu Rev Immunol* 15:617-648.
[202] Scott-Taylor & Dalgleish (2000) *Expert Opin Investig Drugs* 9:471-480.
[203] Apostolopoulos & Plebanski (2000) *Curr Opin Mol Ther* 2:441-447.
[204] Ilan (1999) *Curr Opin Mol Ther* 1:116-120.
[205] Dubensky et al. (2000) *Mol Med* 6:723-732.
[206] Robinson & Pertmer (2000) *Adv Virus Res* 55:1-74.
[207] Donnelly et al. (2000) *Am J Respir Crit Care Med.* 162(4 Pt 2):S190-193.
[208] Davis (1999) *Mt. Sinai J. Med.* 66:84-90.
[209] Parkhill et al. (2000) *Nature* 404:502-506.
[210] Tettelin et al. (2000) *Science* 287:1809-1815.
[211] WO00/66791.
[212] Pizza et al. (2000) *Science* 287:1816-1820.
[213] WO99/24578.
[214] WO99/36544.
[215] WO99/57280.
[216] WO00/22430.

[217] WO00/66741.
[218] WO01/64920.
[219] WO01/64922.
[220] WO03/020756.
[221] WO2004/014419.
[222] WO99/31132; U.S. Pat. No. 6,495,345.
[223] WO99/58683.
[224] Peak et al. (2000) *FEMS Immunol Med Microbiol* 28:329-334.
[225] WO93/06861.
[226] EP-A-0586266.
[227] WO92/03467.
[228] U.S. Pat. No. 5,912,336.
[229] WO2004/014418.
[230] UK patent applications 0223741.0, 0305831.0 & 0309115.4; and WO2004/032958.
[231] Comanducci et al. (2002) *J. Exp. Med.* 195:1445-1454.
[232] WO2004/048404
[233] WO03/063766.
[234] Masignani et al. (2003) *J Exp Med* 197:789-799.
[235] WO2004/015099.
[236] WO02/09643.
[237] Katial et al. (2002) *Infect. Immun.* 70:702-707.
[238] U.S. Pat. No. 6,180,111.
[239] WO01/34642.
[240] PCT/IB2005/003494.
[241] WO99/10497.
[242] WO02/07763.
[243] European patent 0624376.
[244] WO01/52885.
[245] WO00/25811.
[246] Claassen et al. (1996) *Vaccine* 14:1001-1008.
[247] Peeters et al. (1996) *Vaccine* 14:1009-1015.
[248] WO01/09350.
[249] WO02/09746.
[250] Adu-Bobie et al. (2004) *Infect Immun* 72:1914-1919.
[251] WO 02/062378.
[252] WO 2004/014417.
[253] Maiden et al. (1998) *PNAS USA* 95:3140-3145.
[254] http://neisseria.org/nm/typing/mlst/
[255] Pettersson et al. (1994) *Microb Pathog* 17(6):395-408.
[256] Maiden et al. (1998) *PNAS USA* 95:3140-3145.
[257] Welsch et al. (2002) Thirteenth International Pathogenic *Neisseria* Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[258] Santos et al. (2002) Thirteenth International Pathogenic *Neisseria* Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[259] Chen et al. (1956) *Anal. Chem.* 28:1756-1758.
[260] Anderson et al. (1985) *J. Clin. Invest.* 76:52-59.
[261] Costantino et al. (1999) *Vaccine* 17:1251-1263.
[262] Lemercinier and Jones (1996) *Carbohydr. Res.* 296: 83-96.
[263] Gudlavalleti et al. (2004) *J. Biol. Chem.* 279(41): 42765-42773.
[264] Berti F., Bartoloni A., Norelli F., Averani G., Giannozzi A., Berti S. and Costantino P. Congress Presentation—15th Internation Pathogenic *Neisseria* Conference (2006)
[265] Nash (1953) *J. Biochem.* 55:416-421.
[266] Giannini et al. (1984) *Nucleic Acids Res.* 12:4063-4069
[267] Laemmli (1970) *Nature, Lond.* 227:680-685.
[268] Carlone et al. (1992) *J. Clin. Microbiol.* 30:154-159.

The invention claimed is:

1. A saccharide-protein conjugate, wherein the saccharide is a modified *Neisseria meningitidis* serogroup A capsular saccharide wherein at least 90% of the hydroxyl groups at position 3 and at least 90% of the hydroxyl groups at position 4 of the monosaccharide units of the saccharide comprise a blocking group of the formula (Ia):

$$—O—X—Y \qquad (Ia)$$

wherein

X is C(O);

Y is $R^3$; and $R^3$ is $CH_3$, wherein the capsular saccharide comprises four or more monosaccharide units, and an effective amount of the modified capsular saccharide is able to induce a protective immune response in mammals.

2. The conjugate according to claim 1, wherein all the monosaccharide units of the saccharide have blocking groups, at both the position 3 hydroxyl groups and the position 4 hydroxyl groups.

3. The conjugate according to claim 1, wherein the modified capsular saccharide is an oligosaccharide.

4. The conjugate according to claim 1, wherein there is at least one monosaccharide unit of the modified capsular saccharide where two vicinal hydroxyl groups of the saccharide do not comprise blocking groups.

5. The conjugate of claim 1, wherein the protein is a bacterial toxin or toxoid.

6. The conjugate of claim 5, wherein the bacterial toxin or toxoid is diphtheria toxin or toxoid.

7. The conjugate of claim 5, wherein the bacterial toxin or toxoid is CRM197.

8. A pharmaceutical composition comprising (a) the conjugate according to claim 1, and (b) a pharmaceutically acceptable carrier.

9. The composition according to claim 8, further comprising a saccharide antigen from one or more of semigroups C, W135 and Y of *N. meningitidis*.

10. The composition according to claim 8 or claim 9, further comprising a vaccine adjuvant.

11. The composition according to claim 10, wherein the adjuvant is an aluminium phosphate.

12. The composition according to claim 8, which is a vaccine against a disease caused by *N. meningitidis*.

13. A method for raising an antibody response in a mammal, comprising administering the pharmaceutical composition according to claim 8 to the mammal.

14. The composition according to claim 9, wherein the saccharide, in the conjugate, is an oligosaccharide.

15. A molecule comprising a saccharide moiety of formula:

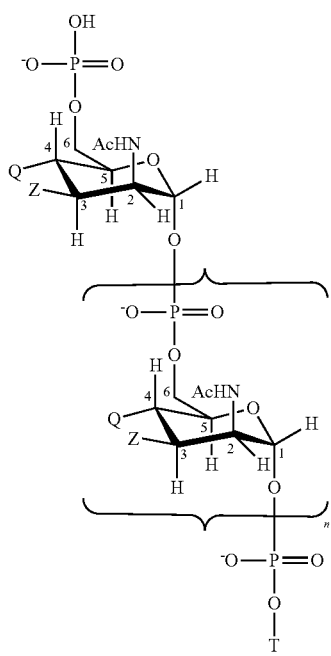

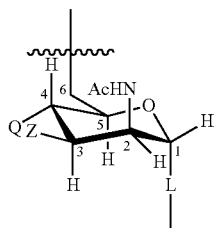

wherein
T is of the formula (A) or (B):

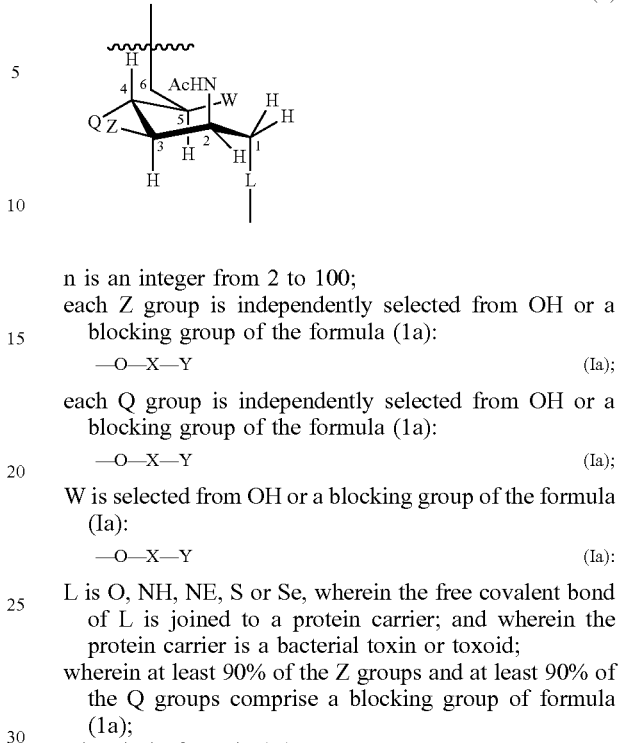

n is an integer from 2 to 100;
each Z group is independently selected from OH or a blocking group of the formula (1a):

—O—X—Y    (Ia);

each Q group is independently selected from OH or a blocking group of the formula (1a):

—O—X—Y    (Ia);

W is selected from OH or a blocking group of the formula (Ia):

—O—X—Y    (Ia);

L is O, NH, NE, S or Se, wherein the free covalent bond of L is joined to a protein carrier; and wherein the protein carrier is a bacterial toxin or toxoid;
wherein at least 90% of the Z groups and at least 90% of the Q groups comprise a blocking group of formula (1a);
wherein in formula (Ia);
X is C(O);
Y is $R^3$; and $R^3$ is $CH_3$.

16. A pharmaceutical composition comprising (a) a molecule according to claim 15, and (b) a pharmaceutically acceptable carrier.

17. The composition according to claim 16, further comprising a saccharide antigen from one or more of semigroups C, W135 and Y of *N. meningitidis*.

18. The composition according to claim 17, wherein the saccharide, in the molecule, is an oligosaccharide.

19. The composition according to claim 16 or claim 17, further comprising a vaccine adjuvant.

* * * * *